United States Patent [19]
Klainer et al.

[11] Patent Number: 5,116,759
[45] Date of Patent: May 26, 1992

[54] RESERVOIR CHEMICAL SENSORS

[75] Inventors: Stanley M. Klainer, Henderson; Johnny R. Thomas, Las Vegas; Marcus S. Butler, Henderson, all of Nev.

[73] Assignee: FiberChem Inc., Las Vegas, Nev.

[21] Appl. No.: 544,681

[22] Filed: Jun. 27, 1990

[51] Int. Cl.$^5$ .................. C12M 1/40; G01N 21/17; G01N 31/2
[52] U.S. Cl. ...................... 435/288; 385/12; 422/82.05; 435/17; 435/26; 436/68; 436/73; 436/79; 436/80; 436/81; 436/83; 436/84; 436/106; 436/109; 436/119; 436/124; 436/135; 436/140; 436/163; 436/536; 436/811
[58] Field of Search ............ 422/82.05–82.011; 350/96.29; 250/227.14; 435/288, 808, 17, 26; 385/12; 436/68, 80, 81, 83, 84, 73, 79, 106, 109, 119, 124, 140, 163, 135, 536, 811

[56] References Cited

U.S. PATENT DOCUMENTS

| | | |
|---|---|---|
| 4,003,707 | 1/1977 | Lübbers et al. |
| 4,810,658 | 3/1989 | Shanks et al. ............... 422/82.05 X |
| 4,865,995 | 9/1989 | Dairaku .................... 422/82.09 X |
| 4,954,318 | 9/1990 | Yafuso et al. ............... 422/82.09 X |

Primary Examiner—Jill Johnston
Attorney, Agent, or Firm—Henry P. Sartorio

[57] ABSTRACT

Single or multi-cell reservoir sensors with single illumination sources and one or more detectors per cell unit have an arrangement whereby a gaseous, vapor or liquid sample enters the cell body and interacts with a sensing solution to detect and quantify a given species. Entrance of the sample into the sensor is through an opening in the cell body which may be covered with a membrane to contain the sensing reagent and to presort the species entering the cell. Reservoir cells can be used with organic, inorganic or biochemical sensing materials. A variety of sensors as alcohol, drugs of abuse, organic halides, cyanide and inorganic ions are provided.

50 Claims, 8 Drawing Sheets

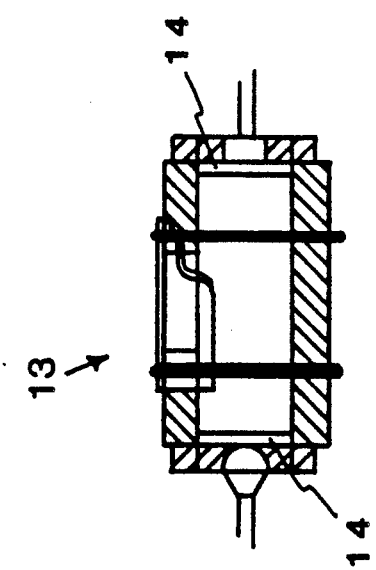
FIG. 3
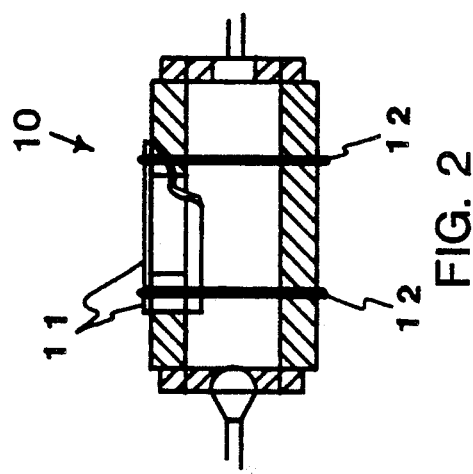
FIG. 2
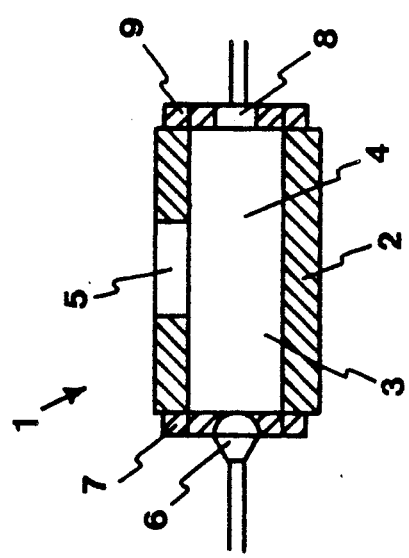
FIG. 1
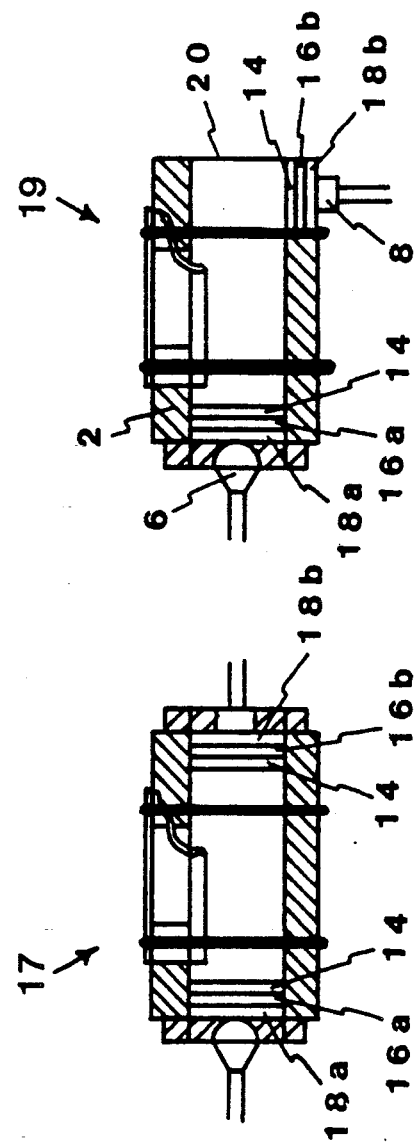
FIG. 6
FIG. 5
FIG. 4
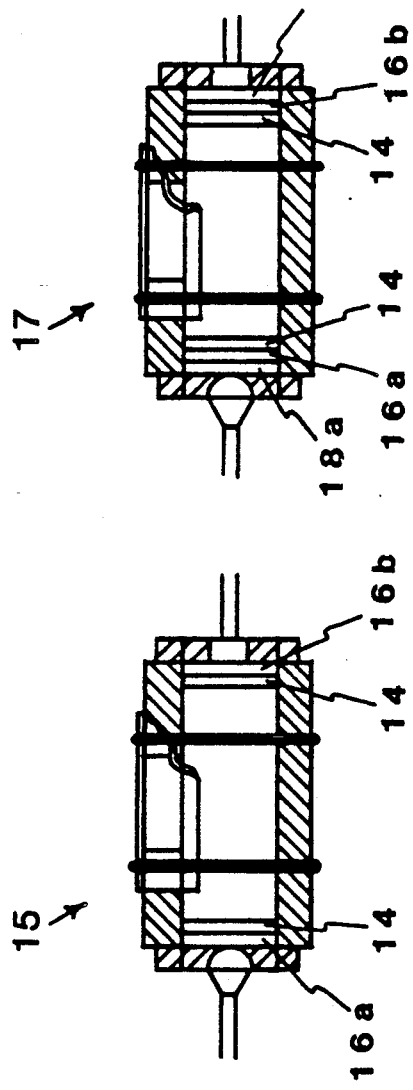

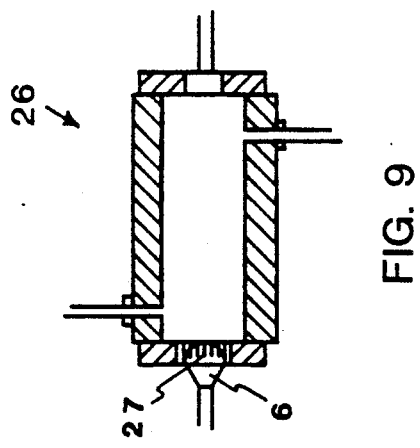
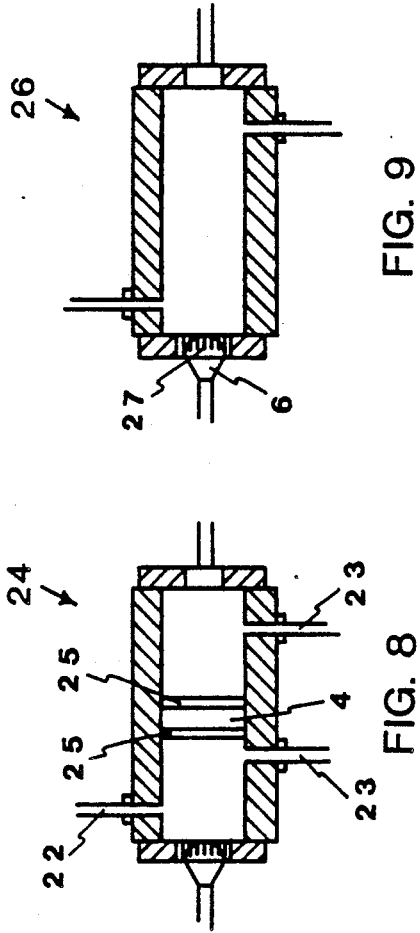
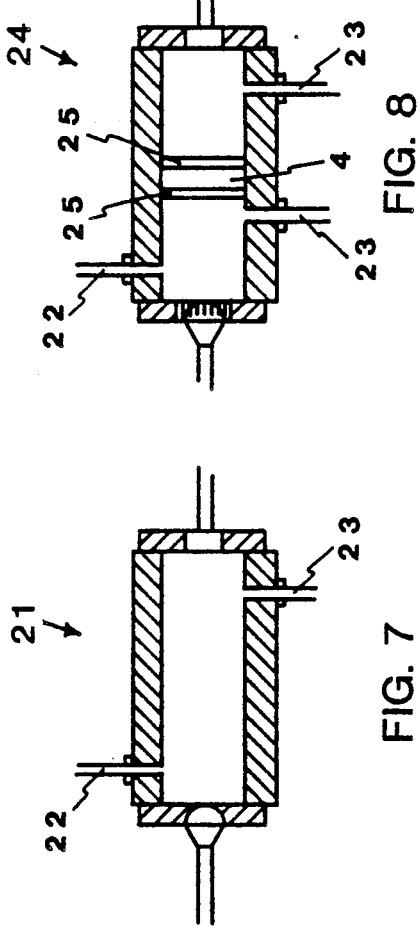
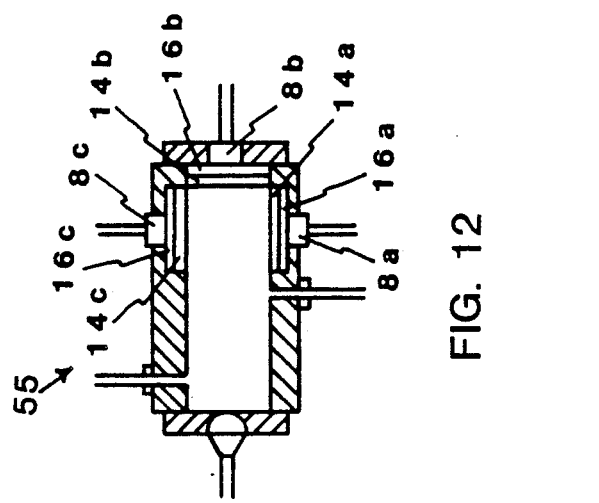
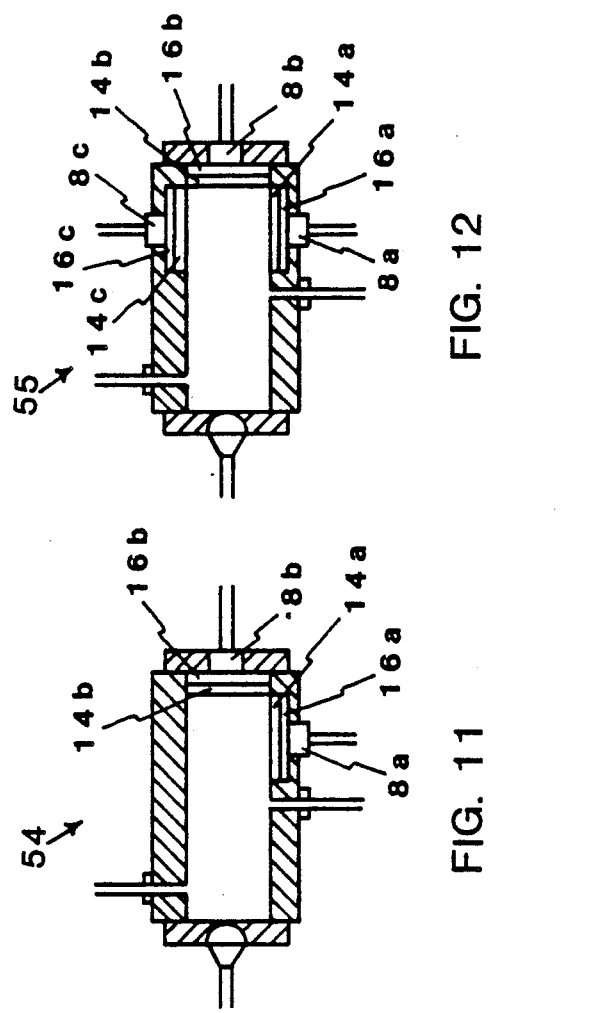
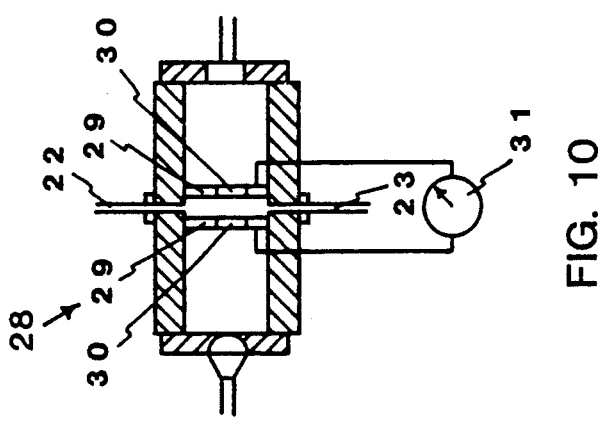

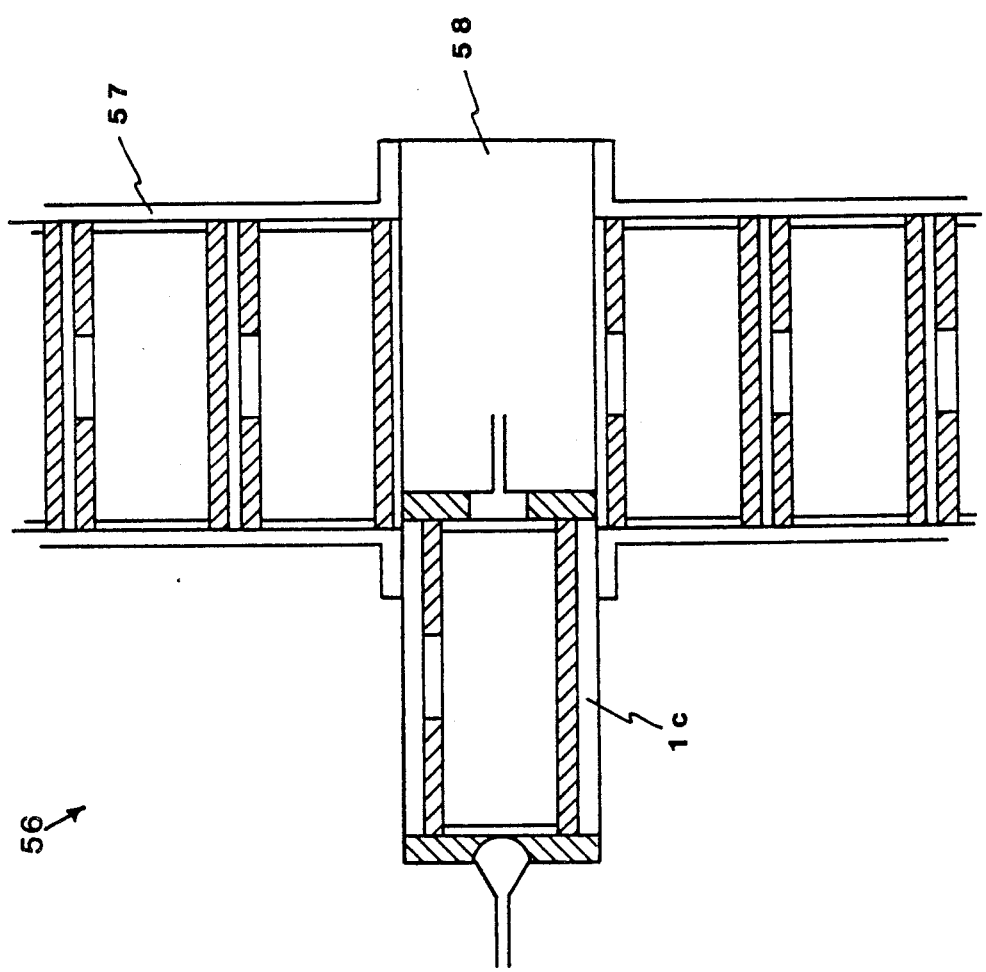

RESERVOIR CHEMICAL SENSORS

BACKGROUND OF THE INVENTION

The invention relates generally to chemical sensors and more particularly to reservoir sensors. This is a universalization of and improvement upon reservoir fiber optic chemical sensors(e.g., U.S. Pat. No. 4,892,383 to Klainer, et al. and U.S. Pat. application Ser. No. 503,464 by Klainer, et al.). This invention embodies measurement techniques, cell design, construction material, membrane selection, and applications.

The need for a universal in-situ sensor capable of working with a variety of light interaction techniques (luminescence, absorption, refection, refraction, Raman and scattering) and using an interminable number of sensing chemistries (organic, inorganic, bio-organic, bio-inorganic and genetic) indicates the desirability of an improved reservoir sensor. This must be coupled with the capacity to perform qualitative and quantitative analysis, high resolution, long active lifetimes (with both reversible and irreversible chemical interactions) and good reproducibility between sensors for a particular species. The sensing reagents are in liquid form (liquids or solids, liquids or gases dissolved in a solvent) and kept in the sensor by species permeable membrane, windows or other leak tight seals. All of the key elements of the sensor should be very accurately controlled. Ideally, reagent solution can be made with a very high degree of repeatability; the active volume can be precisely controlled; the intensity of the illuminating source and the sensitivity of the detector are accurately known; and the size and permeability of the membrane, when used, can be held to good tolerances. Thus, designs are needed which can incorporate all these features and advantages. The reservoir sensor can be of any size or shape, depending on the application. One practical sensor design is a cylinder 3 mm outside diameter and 10 mm outside length. The sensing volume is about 0.03 cc.

Previous emphasis has been placed on reservoir sensors using fiber optics. They have particularly focused on sampling an aqueous environment. Initial fiber optic reservoir sensors have been shown to be inadequate. These include U.S. Pat. Nos. 4,757,343 to Hirschfeld and 4,666,674 to Miller et al. which show typical reservoir FOCS formed by attaching a capillary tube coaxially to the end of an optical fiber using a gas bubble or membrane to close the tube. This structure is laborious to assemble accurately, difficult to control and use and impossible to reproduce uniformly. Another type of FOCS, while not actually a reservoir type, is shown by U.S. Pat. No. 4,478,872 to Peterson et al. wherein a porous polymer jacket or envelope is placed at the end of a pair of fibers and enclosed a fluorescent dye on a solid (particulate) support. U.S. Pat. No. 4,892,383 to Klainer, et al. and U.S. Pat. application Ser. No. 503,463 by Klainer, et al. provide an improved reservoir FOCS having a modular design. Although very practical to construct and uncomplicated to use, its applications are restricted by the use of fiber optics. These cell designs do, however, provide background for this invention. It would be advantageous to provide a more universal sensor design which eliminates the need for optical fibers.

The ability to detect or monitor (identify and quantify) trace amounts of chemical species in situ is of great importance and generally difficult to do. Particular applications include environmental monitoring, pollution control, pollution remediation, prospecting and mining, process control, public health and safety, clinical medicine and industrial monitoring. The improved reservoir sensor has a wide range of capabilities and would be particularly desirable for most of these applications.

Ground water, drinking water, sea water and atmospheric (air) monitoring are very important. The safety of drinking water and the ability of both sweet and sea water to support plant and animal life has become one of the world's key concerns. This, added to the already recognized air pollution problem further complicates the need for monitoring and corrective action. The list of substances that are to be monitored continually increases while, as clinical evaluations continue, the MAC (maximum acceptable concentration) is constantly decreasing. This means that the burden placed on analytical methods is quickly exceeding available specificity and sensitivity. Furthermore, as the accountability for analytical date becomes more demanding, the complexity of the instrumentation and the time to perform an analysis escalates accordingly. When these requisites are considered in light of the fact that there are hundreds of inorganic, organic and biological compounds that are potentially dangerous, toxic or carcinogenic and that there are also supplementary requirements such as pH, turbidity and the amount of coliform bacteria, the need for a simple method of in-situ analyses which can be adapted to many of the targets of interest becomes obvious.

The importance of safe and plentiful ground water supplies cannot be overstated. Domestic water quality is being threatened in many areas of by the intrusion of toxic contaminants into the soil and the ground water form agricultural runoff of pesticides and herbicides; industrial discharge into lakes and rivers; and seepage from solid waste sites (landfills, storage lagoons, and waste piles). Unlike surface contaminants, which are quickly diluted, chemicals in the soil and ground water often remain highly concentrated both underground and in the water which flows from the faucet. The potential magnitude of the problem is enormous. It is, therefore, essential that an economical, practical water monitoring system be in place as soon as possible.

In order to provide adequate protection of water sources, methods for in-situ detection and quantification of low concentrations of toxic contaminants are urgently needed. This includes measuring inorganic, organic and biological species as well as particle count and size. The public health, as well as the public's confidence in domestic water supplies, requires an irrefutable early warning system so that prompt action may be taken to track down the sources of the contamination and to take appropriate steps to protect the public. In order to assure soil and water quality, the contaminants must first be identified, then quantified and remediated, if necessary. Presently, sophisticated stat-of-the-art equipment and methodologies are being used for both diagnostic investigation and monitoring. Wells sometimes must be drilled for proper access to the vadose zone and ground water. Typically, gas chromatography and mass and atomic (absorption and emission) spectroscopy have been used in conjunction with special pumps and samplers to collect the soil and water to be analyzed. Unfortunately, present technologies are not suitable for continuous and widespread monitoring of groundwater contamination. Problems include the contamination of samples by well construction materials; degradation of sample integrity, by most sampling techniques, which could result in questionable data and make enforcement difficult; the high capital investment in complex equipment; and the need for highly skilled technicians. An improved reservoir sensor which is accurate and uniform over a large number of sensors should be the basis for an acceptable, practical diagnostic and monitoring systems.

The need for in situ monitoring of key chemical components in seawater is becoming increasingly more apparent. To develop a better understanding of the parameters which affect ocean flux requires measuring key chemical species as they simultaneously exist in order to obtain time series data. These components are currently measured by collecting water at the site using specially designed water samplers operated from a manned submersible or remotely operated vehicle. These samplers are made of titanium, are expensive, and time consuming to clean and maintain. The water samples are then brought to the surface and analyzed by conventional laboratory techniques to determine the results. Reservoir sensors have the potential to satisfy this monitoring need, which is unattainable with existing instrumentation.

There are presently a very limited number of sensor systems available for commercial use in aqueous systems and virtually none available for use in seawater. Present day methods for the direct measurement of specific chemical parameters in seawater include deployed seawater probes for dissolved oxygen and pH that are based on electrochemistry. These Clark-type probes work either on the galvanic or polarographic principle and have a number of problems including slow response time, reproducibility, chemical and biological fouling of protective membranes, and other effects of high salinity on sensor performance and sensor lifetime. Fiber optic chemical sensors can overcome these problems and will offer many advantages, including batch fabrication at reasonable cost, expendability, small size, light weight and freedom from electromagnetic interference. In FOCS, signals are transmitted optically rather than electrically, which becomes advantageous when handling and deploying long lengths of sea cable in electrically noisy shipboard environments. A reservoir FOCS adapted to these types of measurements will make a groundwater or seawater monitoring system feasible.

Acidity (pH) of surface and ground water is caused by humic acid extracted from swamps or peat beds and by industrial pollution. Excessive acidity causes corrosion which results in many undesirable species entering into the water such as iron, lad and zinc and can be detrimental to fish life. A pH of 0.6 –8.5 is both permissible and desirable in sweet water and 7.0 to 9.0 in seawater.

Arsenic in water is of great concern. Severe toxicity can exist after the ingestion of less than 100 mg of arsenic and chronic toxicity develops with even lower intakes. Arsenic enters the water system from such geological sources as arsenate and arsenite, but it is industrial discharge that increases the arsenic content above safe levels. Although 0.1 ppm is the MAC (maximum allowable concentration) for arsenic, "virtually absent" is the desired level.

Bacteria count is used to determine the sanitary quality of water. Coliform bacteria are normally present in feces, soil and vegetation. It is important to distinguish between fecal and non-fecal coliform since it si the fecal species that is disease producing. The presence of more than 10,000 coliforms per 100 milliliters of water indicates a recent, and possibly dangerous, pollution event. Benzene is one of the most dangerous toxicants. Not only is it a known caricinogen, but it also can cause irritation of the mucous membranes, convulsions and mood changes. Benzene sources include cigarettes, automobile fuels, and industrial processing. The result can be death from cancer or respiratory failure or blood disease. The MAC of 0.005 ppm is probably too high and complete absence is desirable.

Blood in water is of great concern in the vicinity of slaughter houses. Not only can blood transmit a variety of diseases, but it can give water a repugnant taste and also an offensive appearance.

Carbon dioxide has to be measured if there is any hope of understanding the ocean flux process. An in-situ measurement capability for dissolved carbon dioxide in the ocean is an important first steep toward understanding the ocean flux process. This capability is needed by researchers engaged in ocean and global climate studies.

Chlorine is an extremely harmful gas that causes severe lung irritation and damage. The MAC in the air for prolonged exposure is 1 ppm and that for 1-hour exposure is 4 ppm. Brief exposure to 1000 ppm causes rapid death. Chlorine is also the end product from the photolysis of organic chlorides.

Chromium in drinking water is of concern because it is a suspected carcinogen. Chromium exists in two valence states, 3+ and 6+. Of these chromium (6+) is by far the most dangerous. It enters the drinking water from cooling towers, waste water plants, plating operations and the tanning industry. Although the MAC for chromium (6+) is 0.05 ppm, its presence in drinking water above 0.003 ppm indicates the presence of industrial pollution. The complete absence of chromium is the desired level.

Copper content in water should be "virtually absent", although some small amount, 0.1 ppm, is needed for plant growth and body metabolism. If copper is totally absent from drinking water, nutritional anemia may appear in children. Concentrations greater than 0.1 ppm, on the other hand, diminish algae and plankton growth, but at the same time are toxic to several species of fish.

Cyanide is toxic to aquatic organisms at even the lowest levels. The toxicity is due to the liberation of hydrocyanic acid which inhibits oxygen metabolism. Natural waters do not contain cyanide. It comes, primarily, from industrial applications such as metal cleaning and electroplating baths, gas scrubbers and chemical synthesis. It is also a common pollutant in some mining areas. The MAC is 0.01 ppm but the desired level is "absent".

Hydrazine is a violent poison having a strong caustic effect on the skin and mucous membranes. It can lower the metabolism by upsetting certain enzyme systems. The MAC for hydrazine is 5 ppm with a desirable limit of >0.5 ppm.

Iron is not a potential health hazard, but it has the ability to cause pipe encrustation and it causes aesthetic problems, i.e., rust spots on clothing and rust stains in sinks. It also makes the taste of drinking water objectionable. Iron enters the water system by leaching from natural iron deposits or from iron-containing industrial wastes. The soluble form is iron (2+) and the insoluble one iron (3+). The allowable limit is 0.1 ppm iron (2+) and 0.2 ppm iron (3+). The desired level is "virtually absent".

Lead in drinking water arises from any sources such as lead pipes and plastic pipes stabilized by lead. It is toxic to aquatic organisms and accumulates in the human bone structure when more than 300 micrograms per day are ingested. In many situations the actual concentration of lead present is masked by the precipitation of lead chloride and lead carbonate. The allowable lead concentration is 0.05 ppm with "absent" being the desired level.

Mercury may cause nausea, abdominal pain, vomiting, diarrhea and headache. Continuous exposure to mercury could result in inflammation of the mouth and gums, kidney damage, spasms and a change of personality. The MAC is 0.1 ppm with "virtually absent " being the desired level.

Nitrate in water indicates the final stage of water decomposition. High levels of nitrates may indicate biological waste material in the final stages of stabilization or contamination from the run off of agricultural fertilizers. Nitrate also enhances the excessive growth of algae. Since nitrite is changed to nitrates by certain bacteria, the MAC of 10 ppm is for the total nitrate/nitrite concentration. Amounts greater than this can cause cyanosis in infants ("blue babies"). The desired level is "virtually absent".

Oxygen is one of the most important measurements in both sweet and seawater because dissolved oxygen is the best water quality indicator. Dissolved oxygen (DO) is necessary to support all life in the marine environment, and is therefore, the most important water quality parameter. DO concentration is controlled by a process known as oxygen demand. Oxygen demand materials require oxygen for degradation which results in a depletion of ambient DO levels, thereby depriving marine organisms. Man-made wastes, such as sewage, sludge and other forms of organic wastes, are examples of oxygen demand materials. These wastes are also known to cause increased nutrient loading resulting in excessive marine plant growth. It is, therefore, essential to control the amount and type of waste materials dumped into marine waters and to routinely measure and monitor dissolved oxygen to ensure that adequate levels are available to support marine life. Conditions of low dissolved oxygen often occur in highly populated estuarine and coastal areas. Drinking and industrial water should contain at least 4 ppm oxygen but, in general, this must be higher to sustain aquatic life. 8-15 ppm is adequate in both sweet and sea water while air-saturated oxygen is the desired level.

Phosphate is important because in excess it leads to atrophy in lakes. It is also necessary to monitor for phosphate in boiler and cooling towers because it encrusts on the walls. Phosphate gets into the water system from agricultural run off, biological waste, corrosion control materials, detergents and surfactants. The MAC is 50 ppm. Inorganic phosphate must be distinguished from the very toxic organic phosphates which are present in pesticides and chemical agents. These are enzyme inhibitors and can cause death. The MAC for organic phosphates is 0.1 ppm with "completely absent" being the desired level.

Selenium is extremely toxic to humans and animals. It causes inflammation of the lungs and disturbs the digestive and nervous systems. Selenium is a known carcinogen. Its main sources in water are industrial waste and the dissolution of selenium-containing soils. The MAC is 0.01 ppm with "complete absence" being desirable.

Sulfates themselves are not toxic. They do, however, increase the solubility of other very toxic compounds such as lead. They may also lead to diarrhea by forming the laxatives magnesium and calcium sulfates. The MAC for sulfate is 250 ppm with <50 ppm being desirable.

Sulfides are extremely toxic, especially hydrogen sulfide gas. Collapse, coma, and death from respiratory failure can occur within seconds of its intake. It is as toxic as hydrogen cyanide. Fortunately, its obnoxious odor is detectable long before toxic levels are reached. From a pollution stand point, hydrogen sulfide is the by-product of the anaerobic decomposition of organic matter and indicates serious water contamination. The MAC is 0.01 ppm with "complete absence" being the desired amount.

Sulfur dioxide irritates the respiratory system and could cause bronchitis and asphyxia. It may also be an eye irritant causing conjunctivitis. The MAC is 10 ppm with <0.1 ppm being desirable.

Trichloroethylene (TCE) heads the U.S. Environmental Protection Agency (EPA) list of hazardous (toxic, carcinogenic, etc.) compounds and the organic chlorides, as a group dominate the top ten (10) most frequently found dangerous compounds. TCE is of particular concern because it forms the carcinogen, vinyl chloride, in water. Moreover, it is estimated that about 23 million people in the United States are exposed each year to TCE levels ranging from 0.5 to 5 ppm even though 0.005 ppm is the MAC and "absent" is the desired concentration.

The EPA has requirements or is formulating regulations that will require that the above species, as well as others not listed, be continuously monitored. To accomplish this task requires that a device be developed that is both inexpensive to purchase and operate and that can give reliable results in the hands of a moderately trained field technician. Thus the ability to perform the monitoring task (qualitatively and quantitatively) is significant.

In addition to its attributes as an in-situ diagnostic and monitoring device in the environmental area, the reservoir sensor has applications in a multiplicity of other fields. In the law enforcement area reservoir sensors can be used for on-site assessment of drunk drivers and illicit drug users. It could also be used for real-time monitoring of vehicles for smog compliance.

In the medical field, reservoir sensors can be used for blood gas analyses (carbon dioxide and oxygen and pH). Electrolytes (potassium, sodium, calcium, chloride, etc.) are directly measurable with the reservoir sensor. Diagnostics, which presently take hours to days in a laboratory can be done in real time, such as the measurement of creatinine for renal disease; creatine phosphokinase for myocardial infarction; phenylalanine/tyrosine ratio for phenylketonuria; bile acids to evaluate enteroheptic circulation; and appropriate monoclonal and polyclonal antibodies to determine infectious diseases, cancer, AIDS, etc. There are also a variety of industrial application where real-time analysis offer a great advantage such as the control of plating bath composition, the concentration of dissolved rare metals in water to determine the economic viability of recovery, the monitoring and control of the materials in chemical processes, the recovery of the byproducts of chemical synthesis, etc.

SUMMARY OF THE INVENTION

Accordingly, it is an object of the invention to provide a universal reservoir sensor.

It is an additional object to provide reservoir sensors which can be used with luminescence, absorption, reflection, refraction, Raman and scattering techniques.

It is another object of the invention to provide reservoir sensors whose species, or group specific chemistry can be liquids, or solids, liquids or gases dissolved in solvents.

It is also an object of the invention to provide improved reservoir sensor designs which are easy to assemble and which cam be reproduced substantially identically n multiple sensors.

It is further an object of the invention to provide sensor cell designs which can be made out of metal, polymers (plastics), ceramics and glass, or combinations thereof.

It is an another object of the invention to provide sensor cell designs whereby the sensing agent can be removed, the cell cleansed, and new sensing material added automatically without contaminating the sample or the surrounding area.

It is a further object of the invention to keep the sensing chemistry in the reservoir cell by liquid proof seals, membranes, windows or by orienting the cell so no closure is necessary.

It is an additional object to make reservoir sensor designs which use membrane and whose performances are defined by pore size, molecular weight, surface charge, chemical composition or combinations of these.

It is a further object to make sensors which have several reaction chambers separated by membranes so that the sample can react with one or more sensing reagents.

It is another object of the invention to make a flow-through reservoir sensor so that continuous analysis of new sample material is possible.

It is an additional object to make reservoir sensors which have sample preparation chambers to modify the sample before analysis.

It is another object to construct the sensor out of materials which are biocompatible and/or antifouling.

It is an additional object of the invention to provide reservoir sensors for detecting and quantifying gases, vapors and dissolved solids.

It is another object of the invention to provide reservoir sensors for detecting and quantifying inorganic species such as cations, anions and non-ionic species, including the differentiation between valence states such as chromium (3+) from chromium (6+) and iron (2+) from iron (3+).

It is a further objective of the invention to provide reservoir sensors for detecting and quantifying organic species and pharmaceutical products such as compounds, structures and functional groups, including the differentiation between isomers and homologs.

It is an additional objective of the invention to provide reservoir sensors for detecting and quantifying biological species such as compounds of clinical interest, viruses, bacteria, antigens and enzymes.

It is another objective of the invention to provide reservoir sensors for counting and sizing particles in liquid systems.

The invention includes a reservoir cell comprising a modular pass-through reservoir cell body, usually in the shape of a cylinder for optimum illumination, a light source at one end and a detector at the other end. The cell body is filled with a sensing reagent which interacts with a species of interest which passes into the cell body. The light source illuminates the interior of the cell body, and the detector responds to effects produced by the interaction of the species with the reagent. An adapter is provided at each end of the cell so that the source and the detector are properly aligned. The source and detector may be sued to seal the ends of the cell depending on the application and the compatibility of the source and detector material with the sensing agent and the species to be measured. In certain embodiments windows, lenses or both are placed between the source and the cell and the detector and the cell. In other designs, color filters can be placed between the source and the window and the detector and the window or both. It is also possible to place the detector at right angles to the source where it is desired to optimize luminescence response or preserve certain physical properties such as polarization in Raman measurements.

The volume of and the optical path length through the cell body must be accurately known for quantitative analyses. Both of these parameters must be optimized for a particular application. The sample enters the cell through an opening cut into the cell wall. In the basic design a species permeable, sensing reagent impermeable membrane seals the opening cut in the cell. Membrane retainers are attached to the cell body for holding the membrane in place and assuring a liquid tight fit. The membrane holds the reagent in the cell and, at the same time, passes the chemical species of interest through the opening in the cell wall. This permits the sample to interact with the reagent. The source illuminates the interaction and the detector sees the consequence, e.g. fluorescence, absorbance, reflection, refraction, Raman or light scattering. Optical focusing and/or collimating elements such as lenses, mirrors or Winston cones can be easily positioned within the cell, at one or both ends, to optimize sample illumination and signal collection, thereby increasing sensitivity. The cell can be filled through the hole in the cell wall before the membrane is attached. In some embodiments the membrane is attached first and fill holes are provided, one for sensing fluid to be injected and a second for the air in the cell to escape. In a similar fashion automatic filling of the cell can be through one hole and removal of the spent fluid or cleaning solution through the other. For vapor or gas analysis, the membrane can be omitted provided that the orientation of the cell is such that the sensing solution does not spill out. Omitting the membrane is only possible if the sensing chemistry has low volatility so that minimal evaporation occurs. Valid analysis can only occur when the optical path between the illuminator and the detector is completely filled with liquid.

The invention also includes sensor cell designs whereby the species of interest can be pretreated prior to actual analysis. Pretreatment can include creating an excited state, photolysis, radiation, oxidation, reduction, and chemical reaction. This is accomplished by using a flow through chamber placed at the input to the reservoir sensors, generally before the membrane. The source and detector are connected to the cell in an orientation which is substantially orthogonal to the direction of flow through the cell. The flow chamber has inlet and outlet means for flowing, pumping or sucking a gas or liquid sample through the chamber. Excitation, radiation and/or photolyzing sources can be directed into the pretreatment chamber. Reaction chemistries can be placed in the chamber by attaching them to substrates, made of materials such as metal, glass, ceramics and polymers which will not move in the flowing sample stream. The products which result from the reaction of flowing sample with the reactants pass through the membrane and are detected in the reservoir sensors. The products can flow on through and exit the reservoir cell through an opposed membrane or through an exit port into a waste container. A multi-cell configuration in which a plurality of chambers are stacked in series, separated by membranes, can be used.

BRIEF DESCRIPTION OF THE DRAWINGS

In the accompanying drawings:

FIG. 1 shows a basic reservoir sensor.

FIG. 2 shows a basic reservoir sensor with membrane in place.

FIG. 3 shows a basic reservoir sensor with protective windows in front of the source and detector.

FIG. 4 shows a basic reservoir with protective windows and color filters to optimize the illumination source wavelength and to minimize detector response to only the desired wavelength.

FIG. 5 shows a basic reservoir sensor with protective windows, color filters and collimating lenses to optimize the sample area viewed by tailoring the light projection and collection.

FIG. 6 shows a basic reservoir sensor with the detector at right angles to the source to optimize luminescence measurements or to preserve such physical information as polarization.

FIG. 7 shows a basic reservoir sensor with fill and drain ports.

FIG. 8 shows a basic flow-through reservoir sensor with the chemistry contained between two membranes or immobilized on a membrane or porous surface.

FIG. 9 shows a basic flow-through reservoir sensor with an illumination source surrounded by a fiber optic bundle.

FIG. 10 shows a basic flow through reservoir sensor, including an electrically charged channel, for measuring the number and size of particles.

FIG. 11 shows a basic reservoir sensor having tow detectors, one axially aligned with the source and one at right angles.

FIG. 12 shows a basic reservoir sensor having three detectors, one axially aligned with the source and two at right angles.

FIG. 17B shows a stacked array of reservoir sensors.

DETAILED DESCRIPTION OF THE PREFERRED EMBODIMENTS

Figure 13:
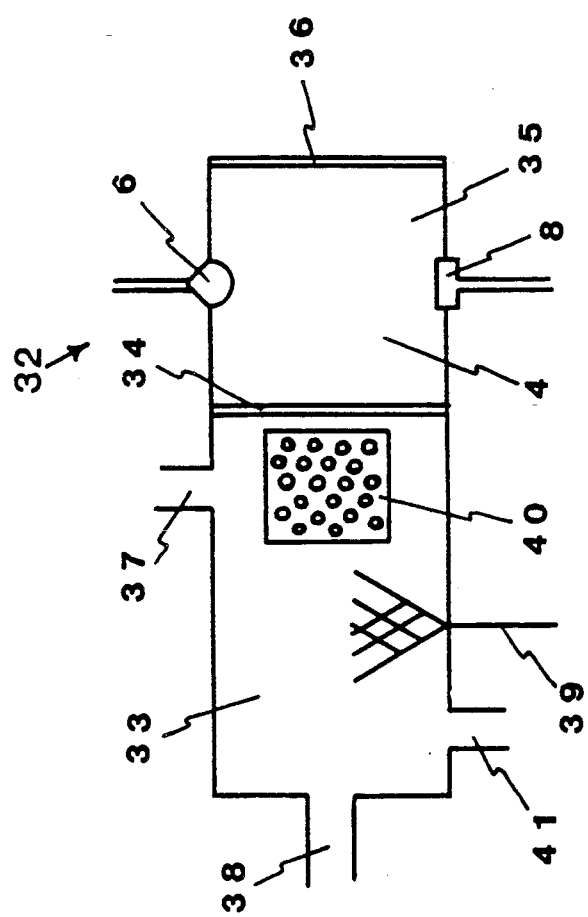
FIG. 13 shows a basic reservoir sensor with a sample preparation chamber attached.

As shown in FIG. 1 reservoir sensor 1 is formed of modular reservoir sensor body 2. The lateral surface of sensor body 2, which is typically cylindrical but may be other shapes, contains species communication means which allows liquids and gases to pass therethrough, e.g., it is porous or has holes formed therein, as will be further described herein. A reaction chamber 3 (channel) formed in the sensor body 2 is filed with a species specific reagent 4. Illuminator (light source) 6 is placed in illuminator adapter 7 which is formed in or attaches to one end of the cell. Adapter 7 makes a liquid tight seal with sensor body 2 and aligns illuminator 6 with detector 8 which is mounted in adapter 9 which is formed in or attached to sensor body 2. Detector adapter 9 makes a liquid tight seal at the other end of sensor body 2 and is used to align detector 8 with illuminator 6. The sensor body 2 has sample opening (port) 5 that allows the species to be analyzed to enter the sensor. The reservoir sensor, as assembled, encloses a predetermined volume which typically contains a known quantity of liquid reagent 4 within the sensor body. The measurement volume is defined by the size of reaction chamber 3. The desired chemical species enter through sample opening 5 into channel 3 of sensor body 2, interact with reagent 4, and produce an effect, e.g. luminescence, absorption, reflection, refraction, Raman or light scattering which is detected by detector 8. The detection apparatus and light sources required to operate the reservoir sensors are known in the art and are shown schematically by source/detector assembly 53, FIG. 16. Illuminator 6 may be a diode, laser or lamp which provides an excitation or input optical signal to the reservoir sensor 1. The reservoir sensor may be a fluorescence sensor or absorption sensor or any other know type of sensor which produces a detectable optical signal which is transmitted through reaction chamber 3 to detector 8. Assembly 53 contains the necessary components to power illuminator 6, operate detector 8 and process, store and transmit the signal form detector 8.

The various reservoir sensors embodiments shown in FIGS. 1-12 all use a similar sensor body 2 as used in the simple embodiment of FIG. 1. The main differences are the addition of other components which tailor each sensor to the species specific chemistry and the intended application.

Although sample opening 5 of FIG. 1, which forms the species communication means to reaction chamber 3, is simply an open port, a more practical sensor requires greater selectivity in passing the species of interest into the reaction chamber and also needs to prevent loss of reagent 4 from the chamber. As shown in FIG. 2, sensor 10 has a semi-permeable membrane 11 covering sample opening 5: membrane 11 is held in place by retaining means 12, e.g., bands or clips, which form a leak proof seal. Membrane 11 is permeable to the species of interest but a sensor cell body, e.g., two openings on opposed lateral side to provide a pass-through flow of the species through the cell, or the lateral surface could be porous. The membrane covers these openings and provides selective communication means through these openings.

Other optical components can be added to the basic cell of FIGS. 1-2, as shown in FIGS. 3-5. As shown in FIG. 3, sensor 13 includes transparent protective windows 14 between the source and detector and the reaction chamber. These may be used when the reagent or species of interest are chemically incompatible with the source and/or detector. The windows are also important in preventing bubbles, as will be further described herein. As shown in FIG. 4, sensor 15 has color filters 16a, b between windows 14 and the source and detector. The filters may be used to select the proper wavelength from a broadband source, or to limit detector response to the desired wavelength. As shown in FIG. 5, sensor 17 further includes a source lens 18a and a detector lens 18b in the optical assembly between the source and detector and the reaction chamber. Lenses may be used to improve the optical efficiency of the cell by optimizing the sample area illumination and collection of a signal at the detector. These components and the like can be used in various combinations as required for the particular application and component characteristics; the illustrations are merely exemplary and not intended to be exhaustive of all possible combinations, e.g., only a single component at either the source or detector end may be used without the other.

In the illustrative embodiments of FIGS. 1-5, the source and detector are at opposite ends of the reaction chamber aligned along a central axis of the reaction chamber/sensor. For some applications, e.g., for Raman or scattering measurements, different alignments are preferable. As shown in FIG. 6, sensor 19 has a source 6 positioned at one end of cell body 2, as before. However, detector 8, although attached at the opposite end of cell body 2, is mounted on the lateral face, not the end face, so that it is aligned at substantially right angles to the central axis of the reaction chamber. Optional windows 14, filters 16a, b, and lenses 18a, b can also be include an necessary. The end 20 of cell body 2 will be a solid wall, or alternatively may be open and covered by additional semi-permeable membrane to increase the area through which the species of interest may pass into the reaction chamber. Alternatively, two or more detectors can be used, one or more positioned as in FIG. 6 and one as in FIGS. 1-5. The axially aligned detector can then be used as a reference for measurements by the other detector(s). The multi-detector embodiments will be further described with reference to FIGS. 11-12.

although a basic ell with membrane can be disassembled to remove the reagent, cleaned, refilled and placed back in use, the need to disassemble and reassemble the cell can be eliminated. As shown in FIG. 7, sensor 21 has a fill port 22 and drain port 23 formed in the cell body. Theseports may be easily opened and closed to allow spent reagent to be drained, cleaning solution to be flushed through, and new reagent to be placed in the cell without any disassembly and reassembly. The sensor isotherwise of the same design as previously described, e.g., membrane type.

The reagent solution need not occupy the entire cell volume. As shown in FIG. 8, sensor 24 has a pair of spaced parallel membranes 25 across the sensor chamber. The volume between the membranes 25 is filled with sensing reagent 4. A fill port 22 and drain port 23 are formed in the cell body on one side of the membrane assembly so that sample may be flowed through one side of the sensor. Membranes 25 are permeable to the species of interest but impermeable to reagent 4. The species of interest thus passes through the first membrane into the reagent and then out through the second membrane. A second drain port 23 is provided in the cell body on the opposed side from the membrane assembly to remove material which passes through the membrane assembly. The indicator material (reagent 4) need not always be in liquid form. The pair of membranes 25 can be replaced with a single membrane or a porous disk on which the indicator material is immobilized, or the indicator material could be coated on the interior walls of the reservoir cell. The sample would then flow in through port 22 and out through port 23.

In place of the lens 18a of FIG. 6, other means can be used to improve the illumination of the reaction chamber. As shown in FIG. 9, sensor 26 has a light source 6 which is surrounded by a fiber optic bundle 27 which collimates the light. This arrangement is useful with a lamp or other light source which is not basically unidirectional.

The sensor cell as heretofore described is used to detect the presence and/or concentration of various chemical species; however, the cell configuration can also be used for other types of measurements. As shown in FIG. 10, a sensor 28 for counting number of particles and/or measuring particle size utilizes the same basic cell body design with light source and detector aligned along the cell body axis. Sensor 28 has a pair of spaced parallel metal plates 29 across the cell. Plates 29 have optically transparent windows 30 at the centers so that there is an optical path from source to detector through the plates. An inlet port 22 and outlet port 23 are formed in the cell body between the plates 29 so that a sample may be flowed through the cell body between the plates. Plates 29 are electrically connected to a charging source 31. The charged plates are used for particle separation.

FIGS. 11-12 show multi-detector arrangements in a reservoir sensor. As shown in FIG. 11, sensor 54 has a pair of detectors 8a, b, one axially aligned with the source and one at right angles. Other components such as windows 14a, b and filters 16a, b may also be included. As shown in FIG. 12, sensor 55 has three detectors, 8a, b, c, one axially aligned with the source and two at right angles. Other components such as windows 14a, b, c and filters 16a, b, c may also be included.

FIG. 13 shows a reservoir sensor 32 with an adjacent sample preparation chamber 33. Chamber 33 can be of any reasonable length. It can be used for liquids, vapors and gases. The reservoir sensor 32 and chamber 33 have a common interface at semi-permeable membrane 34. Membrane 34 keeps sensing reagent 4 in the cell body 35 of sensor 32 while permitting the products of interest from chamber 33 to pass into cell body 35 to interact with sensing reagent 4. A source 6 and a detector 8 are mounted in cell body 35, typically on opposed lateral surfaces. A second semi-permeable membrane 36 in an opposed face of cell body 35 allows the species of interest to cross through body 35 and flow back out, i.e., a cross-flow through the cell. If there is no need for flow out of cell body 35, membrane 36 can be eliminated and replaced by a solid wall (in which the source or detector could be mounted). Chamber 33 is sued where the sample contains a species of interest which cannot be directly or easily measured but can be treated to produce a product which can be more readily detected. Chamber 33 is designed to handle most chemical reactions. The sample enters through sample inlet port 37. Inlet tube 38 admits other reactive gases or liquids which can react with the sample to produce a desired product. Irradiation port 39 provides an opening through which the sample can be irradiated. This includes ultraviolet, visible, infrared, microwave and nuclear excitation. An optional chemical bed 40 in chamber 33 provides a mechanism for liquid-solid and gas-solid reactions to occur with the sample prior to analysis. The species of interest (reaction product) passes through the membrane 34 while the waste sample is removed through outlet port 41. The efficiency of sample preparation can be controlled by the type of chemical reaction chosen, the length of chamber 33, and the flow rate of the sample through chamber 33.

Figure 14:
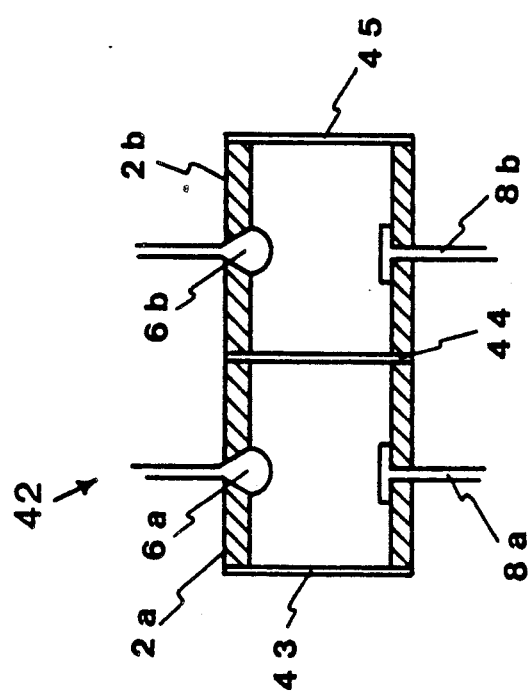
FIG. 14 shows the basic design for a multiple reservoir sensor.

A multiple reservoir sensor can be produced in which a plurality of chambers are arranged in series, separated by semi-permeable membranes. As shown in FIG. 14, multi-reservoir sensor 42 is formed of two modular cell bodies 2a, b joined together with a common membrane 44 at the interface therebetween. The distal ends of each cell body 2a, b from membrane 44 are covered by membranes 43, 45, respectively. Membranes 43, 44, 45 can all be the same or can be of different materials. Each cell body 2a, b is filled with a reagent; the reagents can of course be different. The membranes must be permeable to any species which must pass through the cell while being impermeable to the reagents that are contained in the cells. A light source 6a, b and detector 8a, b are positioned in each cell. As shown, the source/detector are oriented substantially normal to the species flow. The sensor encloses a predetermined volume of a particular reagent in each cell. The species of interest pass through membrane 43 into the first cell, react with the first reagent, and produce an effect which is detected by the first detector. The species, or some product thereof, then passes into the second cell through membrane 44, reacts with the second reagent and produces another detectable effect. Many variations of the above embodiment are possible, e.g., more than two cells can be used, a source and detector may not be required in each cell, and different species communication means than membranes 43, 45 may be used.

Figure 15:
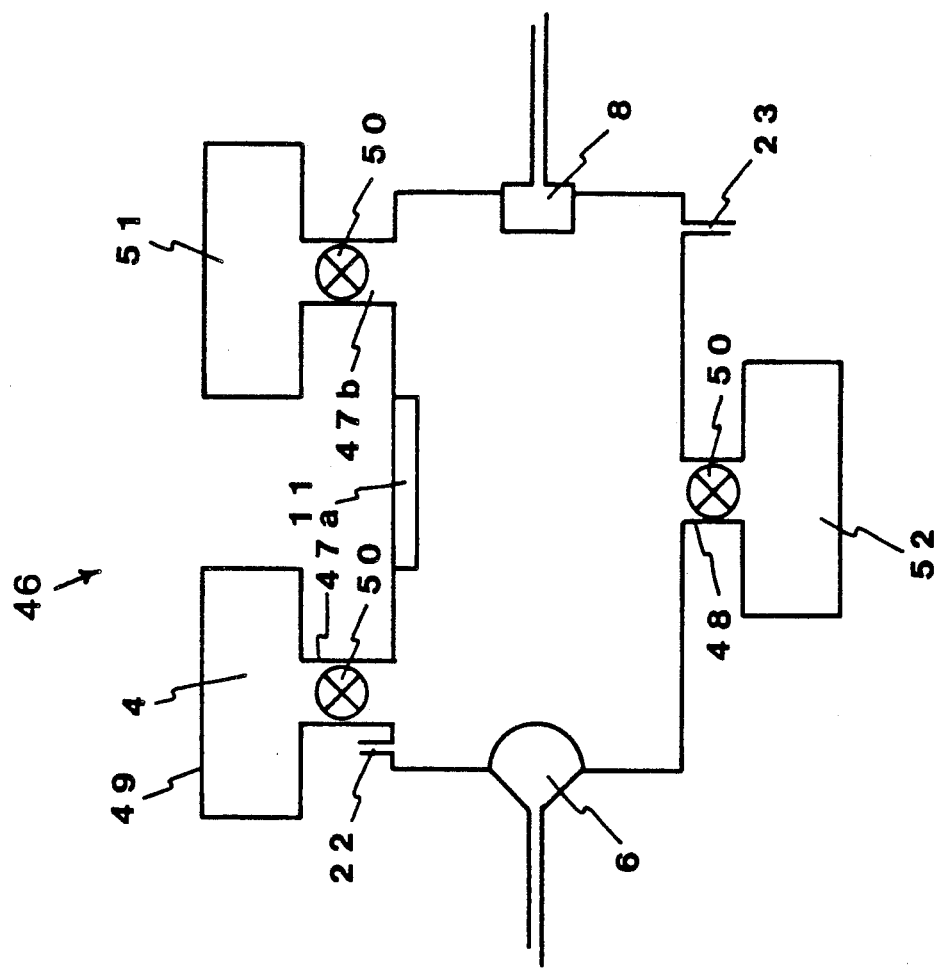
FIG. 15 shows a continuous or pulsed replenishment reservoir sensor.

Other species communication means than an open port or a port covered by a semipermeable membrane as shown in FIGS. 1-6, can also be used, e.g. the inlet and outlet ports of FIGS. 7-9. As shown in FIG. 15 a continuous or pulsed replenishment reservoir sensor 46 is made with the same basic cell body and source/detector arrangement as previously described, with a sample opening and membrane 11 in combination with various ports. A cross-flow through the cell body is produced by lateral sample inlet port 22 and lateral sample outlet port 23. An external reservoir 49 filled with the reagent 4 is connected to reagent inlet port 47a while inlet port 22 is used to input the sample, and the two are mixed in the cell. Outlet port 23, or additional outlet port 48, is used to remove the reagent/sample mixture while the cell is continuously replenished through inlet ports 22, 47a. An additional inlet port 47b may be connected to a reservoir 51 filed with cleaning solution for cleaning the cell when needed. An additional reservoir 52 is connected to port 48 to collect waste. Of course, not all the ports may be necessary in all cell designs. Values 50 placed in the inlet and outlet ports regulate or control flow. Suitable pumps can also be used. Pulsed flow operation is also possible. The flow is substantially transverse to the source 6/detector 8 axis (when the source and detector are positioned in the end faces of the cell) when the inlet and outlet ports are on opposed lateral surfaces of the cell body. Fresh reagent and sample can be continuously flushed through the cell.

Figure 16:
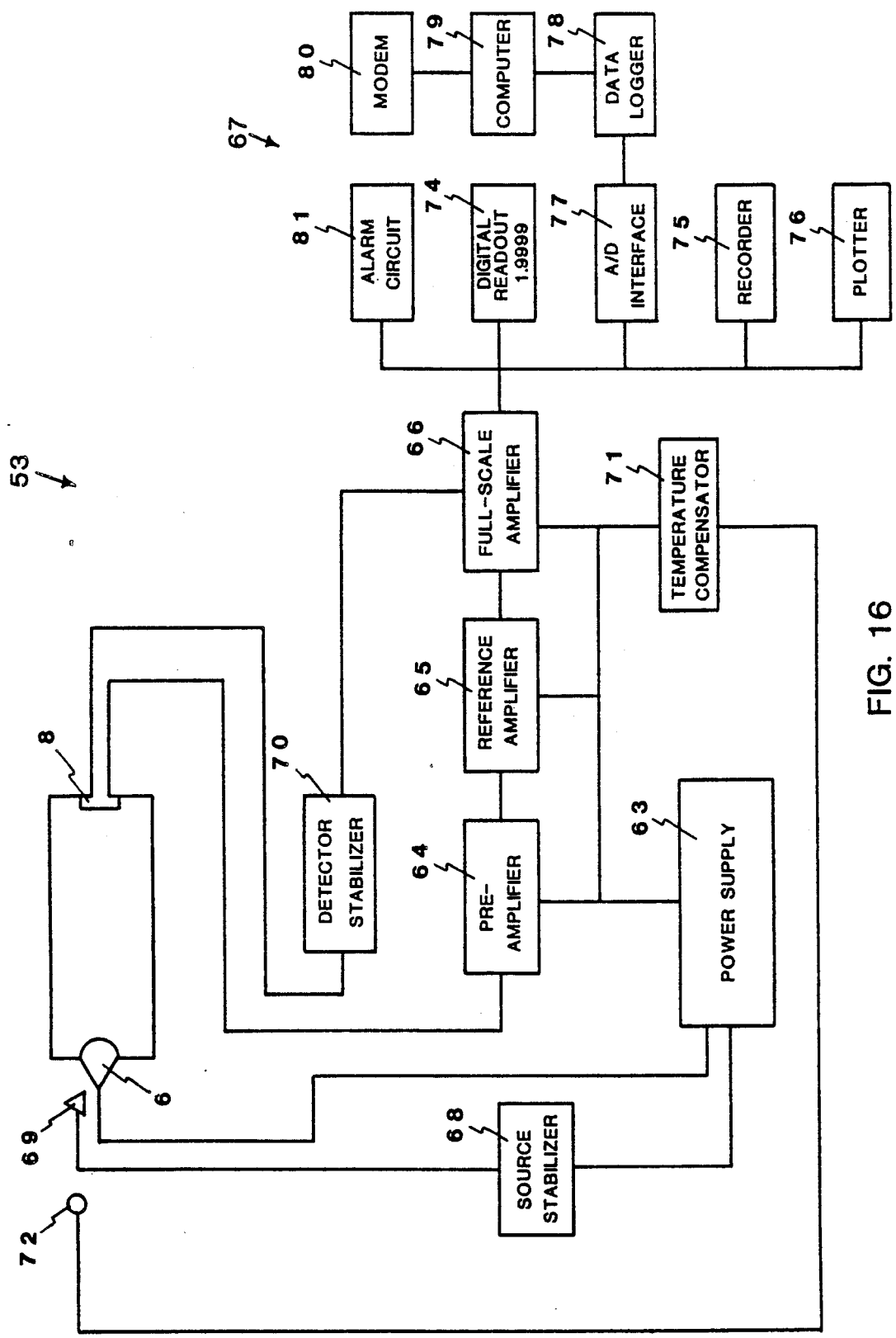
FIG. 16 shows the source/detector assembly for reservoir sensors.

FIG. 16 shows source/detector assembly 53 which is used in conjunction with the reservoir sensor. Light source 6 can be a laser, lamp or diode. Detector 8 detects an optical signal generated in the cell or changes in the input light signal caused by the reaction occurring in the cell. In fluorescence the excitation and detected wavelengths are different whereas in absorption they are the same. The data-containing signal from the detector is processed by assembly 53 to provide analytical information about the species of interest. Detector 62 converts the light intensity into an electrical signal for processing. Detector 62 is selected to have optimum response to the wavelength of the detected light signal. The electronics needed to operate the reservoir sensor consist of power supply 63, pre-amplifier 64, reference amplifier 65, full scale amplifier 66 and readout means 67. Options which improve the stability and data collection ability of the system are also shown in FIG. 16. These may be used individually or collectively. Source 6 is stabilized by measuring its intensity and automatically correcting for variations. Source intensity can be monitored by placing source detector 69 near the source 6. Alternatively source intensity can be measured by detector 8, e.g., when there are multiple detectors in the cell. The signal from detector 69 is fed to source stabilizer 68 which controls the input power to source 6 through power supply 63. Detector 8 is studied by detector stabilizer 70 which feeds-back to amplifier 66. Amplifier 66 then adjusts the sensitivity of detector 8. To assure that there are no adverse temperature effects, temperature compensator 71 is used in connection with a temperature sensor 72. For most situations a thermistor is used as the temperature transducer (sensor) 72. When higher sensitivity or precision is required, the thermistor is replaced with the more temperature sensitive piezoelectric crystal. Readout 67 can be digital display 74 or a variety of recorders 75 or plotters 76. Automated systems include A/D interface 77, date logger 78, computer 79 and plotter 76 and the appropriate software. Data can be obtained from remote sensors sites using modem 80 or a telemetering hook-up. Alarms 81 for instrument failure, changing trends and emergencies are also provided.

Figure 17A:
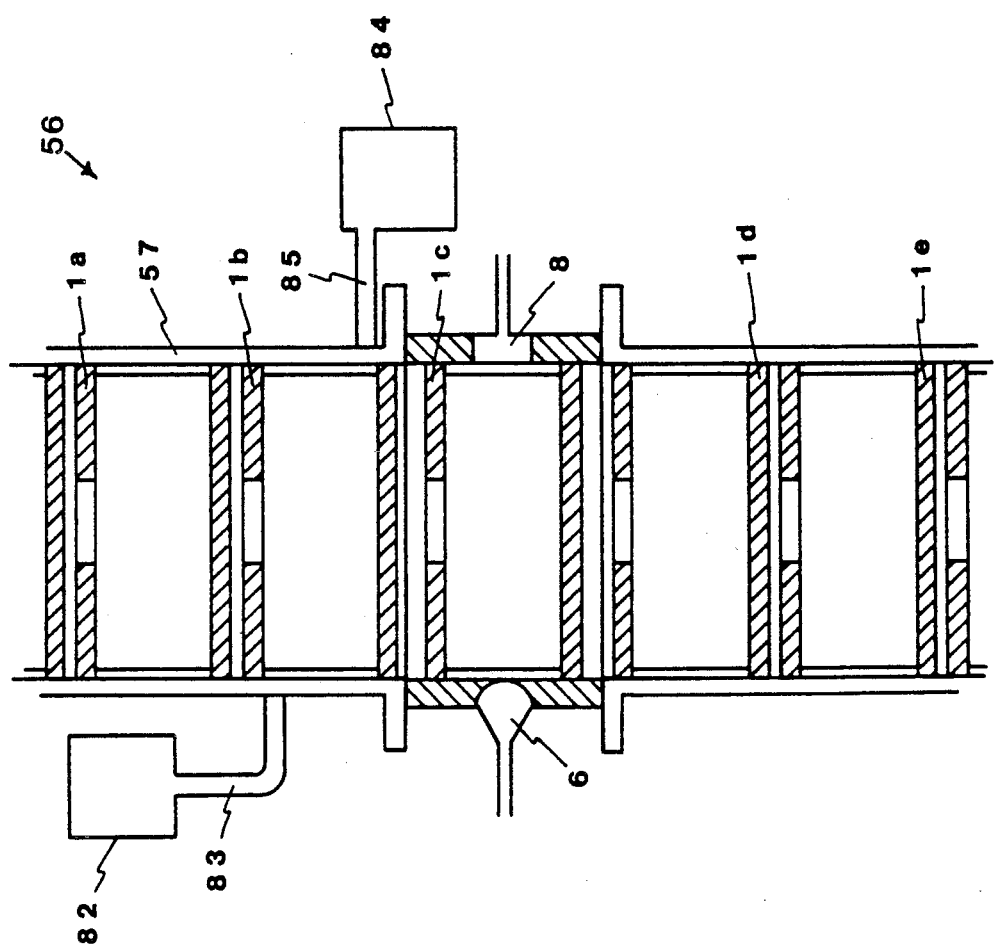
FIG. 17A shows a stacked array of reservoir sensors.

A multi-sensor system for activating, using and discarding a plurality of reservoir sensors is shown in FIGS. 17A, B. The system 56 includes a vertical guide structure 57 which holds a plurality of sensors 1a, b, c, d, e in a stacked arrangement. When a sensor reached the position of sensor 16, the sensor is activated by filling with reagent from reservoir 82 through fill pipe 83. The structure 57 aligns sensor 1; 6 with fill pipe 83 so the filling operation can take place, i.e., a fill port of sensor 1b communicates with pipe 83. A drain port of sensor 16 also communicates with drain pipe 85 which is attached to a reservoir 84 so that air can escape and no bubbles are formed in the fill operation. As the sensors continue to move down the stack, the sensor that was filled moves to the position of sensor 1c where it comes into alignment with a source 6 and detector 8. Sensor 1c where it comes into alignment with a source 6 and detector 8. Sensor 1c can be used for measurement. The measurement may take place in the vertical stack, with the optional feature that sensor 1c could be rotated to position the membrane in a better position to contact the sample (the membrane is preferably at the top during the fill operation). Alternatively, structure 57 may include translation means 58, as shown in FIG. 17B, which allows the sensor 1C (and the source and detector) to be translated horizontally out of the stack for better contact with the sample. After use, sensor 1c moves further down the stack, where it may be cleaned and recycled or may be discarded while a newly fitted sensor moves into the position of sensor 1c. Thus, system 56 keeps a continuous supply of reservoir sensors available for sample measurement.

In accordance with the invention, a miniaturized modular reservoir sensor is produced which is easy and inexpensive to manufacture, rugged, reliable, easy to use, and reproducible uniform. The sensor is small, typically having dimensions of length (optical path-source to detector) of 0.25" to 1.0" and reservoir diameter (inside) of 0.125" to 0.5" and a volume of 10-200 microliters. The cell body is preferably made of acetal theremoplastic polymer, e.g. Delrin, or other plastic polymer, e.g. KEL-F, and should be impervious to water; other materials including metal, ceramics, and glass can also be used. The optimum source and detector will of course depend on the particular measurement being made. A preferred source is a high luminosity, high directivity light emitting diode (LED), with 30-40 microwatts of power; suitable LEDS are available from Sharp. A preferred detector is a GAASP photodiode; suitable photodiodes are available from Hamamatsu.

The active cell volume is dependent on the diameter of the cavity and its length. The optimum diameter is chosen based on the selected operational parameters, e.g., dynamic range, analysis time, active operational life, color of the chemistry, etc. The smallest volume is limited by the minimum practical cell bore and the spacing between the source and the detector. This spacing is critical because the formation of a bubble in the optical path between the source and the detector deteriorates performance. The bubble forms if the surface tension of the sensing solution, the surface energy of the windows in front of the source and the detector (or the faces of the source and the detector) and the spacing between the windows is not optimized. Since the sensing solution is fixed for a particular species, the window material becomes critical when trying to make the optical path length as short as possible. Large cell volumes are also possible with the primary restriction being the ability to properly illuminate the cell. It this situation the source must be sufficiently strong to interact with the sensing solution and optics must be provided to shape the light output of the source so that the optical path is completely and uniformly illuminated and that all of the resultant light is brought to focus on the detector. For a particular species concentration, the larger the cell volume the longer it takes for a light interaction to be recognized. Although there are no limits on cell volume, 10 to 200 microliters have been found to be optimum operating ranges.

It si important that the membrane be placed on the cell in a manner which is compatible with the intended application. The general method of placing the membrane over the cell opening is to attach it to the outer diameter of the sensor wall and hold it in place with retaining rings so that it is liquid tight, i.e., the liquid in the reservoir cannot get out but the liquids and vapors to be analyzed can get in. In many organic systems, such as the TCE chemistry, it is important to keep water out of the cell to prevent hydrolysis. The distance from the membrane to the sensing solution should be dept minimal to reduce reaction time. In reservoir sensors where the cell diameter is equal to or larger than the source/detector diameter, placing the membrane on the outside surface of the sensor is the proper design. If, however, the cell bore is small compared to the total sensor diameter, then it is best to put a recess in the sensor wall so that the distance between the membrane and the sensing solution is minimized. The sample opening 5 of FIG. 1 would be formed in a recessed part of the wall of cell body 2, i.e., the diameter of the outer surface of cell body 2 would be cut down in the area where the opening 5 is formed so the body wall thickness would be minimized and the membrane 11 of FIG. 2 would be close to the interior surface of the cell body wall. Either reservoir sensor membrane design can be used for gas, vapor or dissolved species analysis provided the material suited for individual sample analysis where a drop of the solution to be measured is placed directly on the membrane.

The membrane is a very important part of may preferred embodiments of the reservoir sensor. To perform optimally, i.e., for fast indicator reactions, the membrane must be very thin and must contact the reagent and the sample. It must perform several tasks simultaneously: (i) keep the sensing reagent in the sensor, (ii) pass the species, or classes of compounds, of interest selectively and (ii) prevent potential interferences from getting into the sensor. In the case of the reservoir sensor, therefore, the membrane is defined as nay material which separates the individual components of the sample from the sensor so that reliable quantitative and qualitative measurements can be made. This separation may be accomplished by size, molecular weight, molecular charge, chemical reactions or combinations of these. Several reservoir sensors are based on size separation which is done with membranes of different pore size. This is the most common way to isolate gases and vapors from liquids. Separation of the components in one solution, i.e., the sensing reagent, from the species in a second solution, i.e., the sample, is most commonly done by molecular weight using a dialysis membrane. In situations where neither of these membrane work the options are: (i) put a charged surface on the membrane if the objective is to stop or pass a charged molecule, (ii) put a reactive surface on the membrane which will predictably convert the sample of interest to a species which will transport across the membrane or (iii) prepare the sample in the preparation chamber so that an acceptable species results. In many situations it is easier to work with the sensing reagent than the sample. The minimum hole size or molecular weight membrane that can be used is first defined by the conditions which allow the sample to enter the sensor. If the sample does not reach the sensing reagent there can be no interaction. Under these conditions, sensing reagents may escape from the sensor because they are smaller or of lower molecular weight than the sample. To overcome this problem the sensing reagent is reacted with a compound, such as an inert polymer, to increase its size and molecular weight. When adding to size or molecular weight of the sensing reagent, it is important not to block those chemical groups which specifically interact with the species of interest. In the same manner it is also possible to make a derivative of the sensing agent to give it specific properties, in addition to size and molecular weight, such as charge or additonal species specific active groups.

The most commonly used measurement methods used with the reservoir sensor are: (i) fluorescence, (ii) absorption, (iii) chemiluminescence, (iv) refraction, (v) reflection, (vi) a combination of absorption and fluorescence and (vii) a combination of refraction and fluorescence. The reservoir sensor designs according to the invention can be used with virtually any measurement method and indicator material, including virtually all fluorescer and absorber materials. Fluorescence is a two (2) wavelength system - excitation at one wavelength and emission at another higher wavelength. In addition, many compounds are excited in the blue to ultraviolet wavelength range where the light energy is more energetic. In the general class of fluorescence sensor the light which is used to stimulate the fluorescer molecule generally causes photo-degradation or bleaching of that analyte molecule. This limits the intensity of light which may impinge on this molecule for a given sensor lifetime. The limited light intensity, in turn, limits the fluoresecence signal which may be generated from a sample of fixed concentration because the fluorescence intensity is proportional to the excitation intensity. It is, therefore, desirable to sue the lowest possible source intensity and it is of utmost importance to collect as much of the fluorescence signal as possible and process it optimally. Signal collection depends on the efficiency of the optical system. Lenses can be used as shown in FIG. 5. In addition, by using the optional electronic feed back circuits in source/detector assembly 53 and low noise components, particularly amplifiers, it is possible to process detector signals in the sub-nanowatt range and detect part-per-billion concentrations of most samples.

Absorption spectroscopy is a single wavelength method. Ideally, measurements are made at the same wavelength as the absorption maximum of the species being analyzed. From a practical point of view wavelengths under the absorption band are more than acceptable while wavelengths outside this region will still suffice. In general, since this is not an excitation process such as fluorescence, the sample colors are stable. In addition, absorption measurements are most often made in the visible area of the spectrum where the light is not as energetic as the ultraviolet. Concentrations in the low parts-per-billion range can be detected with a reservoir sensor using absorption techniques.

Chemiluminescence does not have as broad a species coverage as fluorescence or absorption but is very useful for some key compounds. In chemiluminescence a room temperature reaction occurs between compounds that do not emit light to generate fluorescence or phosphorescence. This technique can be used in a sensor in several ways; (i) to detect compounds which generate a unique emission, (ii) to measure biological materials such as bacteria (bioluminescence) and (iii) to analyze species which have specific catalytic effects on the excitation/emission process. No light source is needed since the reaction produces light.

In some situations it is not possible to get a light source at the optimum wavelength, or if a source is available it may not be sufficiently intense or stable. In these situations a fluorophor which emits at the desired wavelength becomes a secondary light source for the measurement. Laser dyes, in particular, make good sources for absorption measurements because they cover the visible spectral region in overlapping increments. By using an excess of fluorophor, the effects of photobleaching are obviated even over extended analysis times. The fluorophor can either be immobilized in the cell or put into the sensing solution (if the sensing solution and fluorophor are chemically compatible). Changes in the amount of fluorescence can be related to sample concentration.

In those circumstances where the sample is colorless, it is possible to make refraction measurements using a fluorophor immobilized in the cell. In this case it is not possible to mix the fluorophor with the sample because this would add color and make it impossible to distinguish between absorption and refraction.

The light intensity received by the sensor varies with the refractive index of the sample and can be used to measure the amount of species present. This technique can be used for liquid, vapor or gas samples. In the case of a liquid sample the fluid inside the sensor can be the same as the sample if impurities are the analytical target. If the liquid itself is to be measured then a solvent is placed in the sensor. If part of a liquid sample is to be analyzed the solvent in the sensor is chosen so that the species of interest partition into the sensor. Vapors and gases can cross directly into the sensor and be measured or they can be dissolved in a calibrated solvent and analyzed.

Although the reservoir sensor is primarily a qualitative and quantitative monitoring device for pollutants and trace species in air, sweet water and sea water, this type of efficient, small size, simple measurement system has many uses. These application include: (i) simplified fluorescence and absorption spectrometers for testing laboratories, (ii) absorption detection units for high pressure liquid chromatography (HPLC) where the difficulties of designing detector sensor using bulk optics are substantial, (iii) flow sensor for flow injection and continuous flow analyzers, (iv) small sampling heads for process stream analyzers in production facilities, (v) determination of sensor population in biological broths and (vi) in-vitro measurement of species of medical interest. In each of these ares the sensor allows the optical sampling sensor to be placed at some location which is optimized for the analysis rather than at a location which is optimized for bulk optics placement. Thus, connecting flow tubes to the sensor can be minimized, in turn, minimizing dead volume and analyte band broadening.

The reservoir cell is uniquely qualified for use with multiple detectors. One to three detectors are optimum although more can be sued if the cell size is large enough to accommodate them. In the simplest embodiment a single detector is sued either opposite the light source (usually absorption, light scattering, etc.) or at right angles tot eh light source (usually luminescence, Raman, etc.). The purpose of using two detectors is to provide for a sample signal and a reference signal or for two different sample signals. In one application, if the sample signal is fluorescence and the species specific reagent solution is colored, the detector opposite the illuminating source can be used to correct for any fluorescent light that is absorbed by the colored solution. In another embodiment, if in an absorption reaction there is an isosbestic point, i.e., where all of the curves intersect, this can be used as a reference signal to correct the absorption signal for instrument and cell variations. If three detectors are used, then it is possible to look at a reference and two different signals, i.e., two different spectral wavelengths, and a reference. In the chlorine reservoir sensor, as an application, at one wavelength peak intensity decreases as sample concentration decreases, there is an isosbestic point and at a second wavelength peak intensity increases as sample concentration decreases. With three detectors, both wavelengths and the isosbestic point can be monitored and ratioed for high precision measurements. In all multiple detector systems, the big advantage is that there is a reference, independent of the chemical interaction with the sample, which can be used to correct for instrument and sensor anomalies. The use of multiple detectors means the use of electronics with not only multiple detector capability, but with circuitry to properly interface one signal with another, e.g. ratio, add, subtract, etc.

One specific type of reservoir sensor is a pH sensor. The pH sensor is formed using a hydrogen ion/hydronium ion (H+/H3O+) permeable membrane and the reservoir sensor is filled with a reagent solution which reacts with hydrogen ion/hydronium ion which permeates through the membrane. The sensor is illuminated by an input or excitation signal from the light source and an output signal is produced whose intensity can be related to pH.

Absorption and luminescence quenching are the bases for the reservoir sensor pH sensor. Several pH sensitive absorption dyes such as phenol red, cresol red, methyl violet, congo red, phenolphthalein, and bromcresol purple can be sued in absorption or in fluorescence in conjunction with a pH insensitive fluorophor such as eosin. Either of these techniques are applicable to all dyes that change color as function of pH. Dye concentrations are $10^{-2}$ molar while the eosin is $>10^{-4}$ molar. Direct fluoresecnece measurements using fluorescein, acridine, umbelliferone and beta-naphthol at between $10^{-5}$ molar can also be sued if excitation power can be kept below the photodecomposition level. A reagent solution of either of these types of reagents can be placed in the reservoir sensor. A dialysis membrane of MWCO (molecular with cut off) 100 is sued to keep the reagents int eh sensor while passing the hydrogen ion/hydronium ion. For the absorption dyes eosin can be excited at 488 nm and its emission peak appears at 566 nm. This is an ideal wavelength range to work in. Phenol red covers pH range 6.8 to 8.4, cresol red 7.2 to 8.8, methyl violet 0.1 to 1.5, congo red 3.0 to 5.2, phenolphthalein 8.2 to 10.0 and bromocresol purple 5.2 to 6.8. Fluorescein is an example of a fluorescent dye. It can be excited at 488 nm and it emission peak is at 545 nm. In solution fluorescein responds to pH range 4.0 to 6.8. This technique is applicable to all pH sensitive dyes which change color or fluoresce.

Another specific type of reservoir sensor is an arsenic sensor. The arsenic sensor is formed using an arsenic ion permeable membrane and the reservoir sensor is filled with a reagent solution which reacts with the arsenic ion. The arsenic ion permeates through the membrane. The sensor is illuminated by an excitation signal from the light source and an output signal is produced whose intensity can be related to arsenic ion concentration.

Absorption or luminescence quenching is the basis for the reservoir sensor arsenic ion sensor. A reagent solution of either ammonium molybdate and stannous chloride or N-ethyl-8-hydroxtetrahydroquinoline and ferric chloride can be placed in the reservoir sensor. A dialysis membrane of MWCO (molecular weight cut off) 100 is used to keep the reagents in the sensor while passing the arsenic ion. The ammonium molybdate/stannous chloride gives a blue color with arsenic ion whose intensity is dependent on arsenic concentration. This is measured in absorption at 450 nm. The N-ethyl-8-hydroxtetrahydroquinoline/ferric chloride gives a red-brown color with arsenic ion and is detected in absorption at 600 nm. These reactions can also be measured in fluorescence by using eosin immobilized on a fiber optic inserted into the sensor and exciting at 488 nm and detecting at 546 nm. The loss of fluorescence intensity at the detector due to color formation can be related to arsenic concentration. Both the ammonium molybdate/stannous chloride and N-ethyl-8-hydroxtetrahydroquinoline/ferric chloride solution have limited shelf-lives. To improve this the individual components of the solution are separated into a two-cell reservoir sensor, FIG. 14. The arsenic solution, in this configuration, first enters the ammonium molybdate solution and reacts. The resultant product, arsenomolybdate, then passes through the second membrane into the second sensor where the stannous chloride is stored. When this happens the blue color is formed. This can also be done with the N-ethyl-8-hydroxtetrahydroquinoline in the first sensor and the ferric chloride in the second. Other arsenic sensors utilize fluorescence quenching of thorium-morin chelate or a butylrhodamine B/chloride mixture, and chemiluminscence of a luminol-$(NH_4)_2MoO_4$-$NH_4NO_3$ mixture. The reagents are placed in a sensor, and the resulting effect of arsenic is detected.

Another specific type of reservoir sensor is a benzen sensor. The benzene sensor is formed using a benzene permeable membrane. Care has to be taken that this membrane does not dissolve or lose its separative properties in benzene. The reservoir sensor is filled with a solvent for benzene whose refractive index is much smaller than benzene. Benzene permeates through the membrane and is collected in the solvent. The sensor is illuminated by an excitation signal from the light source and an output signal is produced whose intensity can be related to benzene concentration.

Benzene is determined suing a combination of refractive index and fluorescence. The sensor is filled with a compound with a lower refractive index than benzene (Refractive index 1.50) in which benzene is soluble, e.g., ethanol (refractive index 1.36) or acetone (refractive index 1.36). The benzene permeable, benzene/solvent insoluble membrane is a polymer, e.g., high density polyethylene, high density polypropylene or fluorinated or surface fluorinated forms of these). The cell interior is coated with a fluorophor immobilized in a benzene insoluble matrix. The signal obtained for pure solvent is used as the baseline. AS benzene dissolves in the solvent the refractive index of the solvent increases, changing its light transmission characteristics. The differences in the intensity of light signal received at the detector between the baseline (pure solvent) measurement and the solvent containing benzene can be related to benzene concentration.

Another specific type of reservoir sensor is a cyanide sensor. The cyanide sensor is formed using a cyanide permeable membrane and a sensing reagent specific to cyanide. Cyanide permeates through the membrane and is collected in a solution of the species specific sensing reagent. The sensor is illuminated by an excitation signal from the light source and an output signal is produced whose intensity can be related to cyanide concentration.

Cyanide is determined using luminescence. The sensor is filled with p-benzoquinone which specifically reacts with cyanide to form 2,3-dicyanoquinone. The benzoquinone if held in the sensor with a membrane of MWCO 100. Luminescence excitation is at 450 nm and emission is at 500 nm. The fluoresecence of the venzoquinone changes its light transmission characteristics. The differences in the intensity of light signal received at the detector between the base line (p-benzoquinone) measurement and the increase in fluorescence as the 2,3-dicyanoquinone is formed can be related to cyanide concentration.

Another specific type of reservoir sensor is a hydrazine sensor. The hydrazine sensor is formed using a hydrazine permeable membrane and a sensing reagent specific to hydrazine. Hydrazine permeates through the membrane and is collected in a solution of the species specific sensing reagent. The sensor is illuminated by an excitation signal from the light source and an output signal is generated whose intensity can be related to hydrazine concentration.

Hydrazine is determined using absorption The sensor is filled with cupric neocuproine solution which specifically reacts with hydrazine to form a yellow solution. The more hydrazine the darker the solution. The cupric neocuprione is held in the sensor with a membrane of MWCO 100. The absorption of light at 450 to 458 nm is pure neocuprione is used as a baseline. More absorption occurs as hydrazine enters the sensor. The increase in absorption can be related to hydrazine concentration.

Another specific type of reservoir sensor is a cupric ion sensor. The copper sensor is formed using a cupric ion permeable membrane and a sensing reagent specific to copper. Cupric ion permeates through the membrane and is collected in a solution of the species specific sensing reagent. In one embodiment of the copper sensor the sample is excited by light from the light source while in a second system the reaction of the sample with the reagent generates light. An output signal is generated whose intensity can be related to copper concentration.

Cupric ion is determined using either fluorescence or chemiluminescence. In one system the sensor is filled with 2,2'-dipyridylketone hydrazone solution which specifically reacts with copper. The 2,2'-dipyridylketone hydrazone solution is held in the sensor with a membrane of MWCO 100. The fluoresecence of the 2,2'-dipyridylketone hydrazone is quenched by copper in a manner which can be directly related to cupric ion concentration. In another approach the sensor is filled with lumocupferron solution. This is kept in the sensor with a membrane of MWCO 100. Copper specifically catalyzes the chemiluminescence of lumocupferron. The intensity of the self-emitting light can be directly related to copper concentrations. One of the advantages of this chemiluminescence reaction is its sensitivity, <1 ppb.

Another specific type of reservoir sensor is a Trichloroethylene (TCE) sensor. The TCE sensor is formed using a TCE permeable membrane. Care has to taken that this membrane does not dissolve or lose its separative properties in TCE. The reservoir sensor is filled with a solvent for TCE whose refractive index is much smaller than TCE. TCE permeates through the membrane and is collected in the solvent. The sensor is illuminated by an excitation signal from the light source and an output signal is produced whose intensity can be related to TCE concentration.

TCE is determined using a combination of refractive index and fluorescence. The sensor is filled with compound with a lower refractive index than TCE (refractive index 1.48) in which TCE is soluble, e.g., ethanol (refractive index 1.36) or acetone (refractive index 1.36). The TCE permeable, TCE/solvent insoluble membrane is a silicone polymer. These are chosen because they selectively pass chlorinated hydrocarbons thus adding specificity to the analysis. The cell interior is coated with a fluorophore immobilized in a TCE insoluble matrix. The signal obtained for pure solvent is used as the baseline. As TCE dissolves in the solvent the refractive index of the solvent increases changing its light transmission characteristics. The differences in the intensity of light signal received at the detector between the baseline (pure solvent) measurement and the solvent containing TCE can be related to TCE concentration.

Another specific type of reservoir sensor is a mercuric ion sensor. The mercury sensor is formed using a mercuric ion permeates membrane and a sensing reagent specific to mercury. Mercuric ion permeates through the membrane and is collected in a solution of the species specific sensing reagent. In the mercury sensor, the sample is excited by light from the light source and an output signal is generated whose intensity can be related to mercury concentration.

Mercuric ion is determined using "heavy metal" fluorescence quenching. In one system, the sensor uses 2,2'-dipyridylketone hydrazone solution which specifically reacts with mercury. The 2,2'-dipyridylketone hydrazone solution is held in the sensor with a membrane of MWCO 500. The fluorescenece of the 2,2'-dipyridylketone hydrazone is quenched by mercury in a manner which can be directly related to mercuric ion concentration. Since may metals quench 2,2'-dipyridylketone hydrazone, its specificity is obtained by proper selection of the excitation and emission wavelengths. The decrease in fluorexcence intensity can be directly related to mercuric ion concentration. Another mercuric specific reagent is indole-3-propionic acid. This is also kept in the sensor with membrane of MWCO 500. Mercury predictable quenches the fluorescence of indole-3-propionic acid so that the intensity of the light emission can be equated to mercuric ion concentration.

Another specific type of reservoir sensor is an iron (2+) sensor. The iron(2+) sensor is formed using an iron (2+) permeable membrane and a sensing reagent specific to iron (2+). Iron (2+) permeates through the membrane and is collected in a solution of the species specific sensing reagent. In the iron (2+) sensor, light enters the sample from the light source, interacts with the sample, and an output signal is generated whose intensity can be relate to iron (2+) concentration.

Iron(2+) is determined using absorption. The sensor uses ferrozine solution which specifically reacts with iron (2+). It does not respond to iron (3+). Ferrozine is very light yellow is solution. It turns various densities of purple when exposed to different concentration of iron (2+). The ferrozine is kept in the sensor with membranes of either MWCO 100 or 500. The ferrozine absorbs the input light in a predictable manner so that light loss, or the percent of light absorbed, can be used to determine iron (2+) concentration. At low ppm and ppb iron (2+) concentration, light intensity is linear with iron (2+) concentrations.

Another specific type of reservoir sensor is a chromium (6+) sensor. Chromium (6+) is detected by an absorption measurement using bis (2,4,6 trichlorophenyl) oxalate-$H_2O_2$-per-5ylene or acidified diphenylcarbazide as the reagent. Chromium (6+) can also be detected by chemiluminescence of a lophione-KOH-$H_2O_2$ mixture.

Another specific type of reservoir sensor is an alcohol sensor which would be particularly useful to law enforcement agencies. Alcohol can be detected by absorption using acidified vanillin as the reagent in the reservoir cell. The vanillin turns red int eh presence of alcohol, so the intensity of the red color formation is a measure of the amount of alcohol present. Alcohol can also be detected by fluorescence using a mixture of alcohol deghyrogenase and zinc hydroxide as the reagent in the reservoir cell. The alcohol undergoes a reversible oxidation to convert AND+ to NADH and the resultant fluorescence intensity is a measure of the amount of alcohol present.

Another specific type of reservoir sensor is a sensor for aldehydes. Aldehydes can be detected by fluorescence using p-nitrophenyl hydrazine as the reagent.

Another specific type of reservoir sensor is a sensor for blood. Blood can be detected by absorption using benzendine or tetramethyldiaminotriphenylmethane as the reagent.

Another specific type of reservoir sensor is a chlorine sensor. Chlorine can detected by absorption using congo red as the reagent, or by fluorescence using flyuorescein as the reagent. In addition to the basic ell for detecting chlorine gas, the reservoir cell can be used in combination with a pretreatment chamber, as shown in FIG. 13, to detect organic chlorides. The organic chloride is photolyzed in the pretreatment chamber to produce chlorine which passes through the membrane into the reservoir cell for detection.

Another specific type of reservoir sensor is an ozone sensor. Ozone can be detected by fluorescence using dihydroacridane as the reagent; the dihydroacridane reacts with ozone to produce acridine orange, which fluoresces when excited by the light source. Ozone can also be detected in a reservoir cell by absorption using indigo blue as the reagent. The indigo blue turns from blue to colorless in the presence of ozone.

Another specific type of reservoir sensor is a selenium sensor. Selenium can be measured by fluorescence quenching in a reservoir cell using 2,3-diaminonaphthalene or 3,3'diaminobenzidine or dithizone as the reagent. The fluorescence of the reagent produced by the illumination source is quenched by the presence of selenium.

Another specific type of reservoir sensor is a silver sensor. Silver is measured by fluorescence quenching in a reservoir cell using 2,3 napthotriazole or a 1, 10 phenanthroline/eosin mixture as the reagent.

Another specific type of reservoir sensor is a gold sensor. Gold is measured by fluorescence quenching of a butrylrhodamine B/chloride mixture or 5-hydroxy-2-hydroxmethyl-1,4-pyrone reagent.

Another specific type of reservoir sensor is a calcium sensor. Calcium is detected an quantified by fluorescence of N-(4-methylumbelliferone-8-methyl)-1,10-diazo-18-crown-6.

Another specific type or reservoir sensor is a sulfite sensor Sulfites are detected and quantified by absorption using malachite green as the reagent. Sulfites convert malachite green to leucomalachite green, changing the color from green to colorless. The color change is detected by an absorption measurement.

Another specific type of reservoir sensor is a sulfate sensor. Sulfates are detected by absorption in a reservoir cell using red thorin-barium complex as the reagent. The reagent turns from red to yellow in the presence of sulfates.

Another specific type of reservoir sensor is a creatine phosphokinase sensor, which is used to detect heart disease. A mixture of MM and BB monclonal antibodies and MB polyclonal antibody is tagged with a fluorescent compound, e.g. fluorescein or rhodamine B, and placed in the reservoir cell, either as a reagent solution or immobilized in the cell. A competitive assay takes place in the presence of cratine phosphokinase, resulting in fluorexcnce loss. In a competitive assay, a tagged antigen is attached tot eh antibody which is sued as the indicator. The untagged antigen (species to be detected) displaces the tagged antigen on the antibody, causing a loss of fluorescence with is a measure of the amount of untagged antigen present.

A reservoir sensor using antibodies can be used to detect various antigens: An antibody specific to a particular antigen is placed in the reservoir cell, either in a reagent solution or immobilized in the cell. For example, antibodies specific to cocaine, caffeine, chlordane, methadone, morphine, hepatitis (A and B), herpes (various types) and influenza (various types), can be used in a reservoir cell. Cancer may be detected using an antibody specific to a know cancer indicator.

A reservoir sensor can also be based on enzymes. The enzyme 3α-hydroxysteroid dehydrogenase can be used for total bile acids while selected hydroxysteriod hydrogenases are used for specific bile acids. Pyruvate dehydrogenase is used for pyruvate; aldehyde dehydrogenase is sued for aldehydes; cholesterol dehydrogenase is used for cholesterol. In the enzymatic assays, the reservoir sensors, particularly the multiple reservoir design, is suitable for use of coenzymes as well as the use of coupled assays.

The above-described preferred embodiments of the invention are not intended to be exhaustive of all possible reservoir sensors. In accordance with the invention, different reservoir sensors can be designed which are specific to a wide number of particular species, using any known fluorescer or absorber or other known detection mechanism which can be carried out in a reservoir sensor. Although the illustrative examples have been primarily described with reference to embodiments which use a semi-permeable membrane to selectively transmit the species of interest, other embodiments which do not use a membrane, as previously described, could also be sued. These other embodiment would use the same reagent and same measurement techniques.

Changes and modifications in the specifically described embodiments can be carried out without departing from the scope of the invention which is intended to be limited only by the scope of the appended claims.

We claim:

1. A reservoir chemical sensor comprising:
   a modular reservoir cell body made of acetal theremoplastic polymer;
   a sensing reagent in the cell body;
   species communication means formed in the cell body for passing a species of interest into the cell body to interact with the sensing reagent.
   a light source positioned at one end of the cell body to illuminate the interior of the cell body;
   a detector positioned at an opposed end of the cell body to detect effects produced by the interaction of the species of interest with the sensing reagent;
   an adaptor means at each end of he cell for mounting and aligning the light source and detector to the cell body.

2. The sensor of claim 1 wherein the sensing reagent is a solution filling the reservoir cell body.

3. The sensor of claim 2 further comprising a transparent, protective window between the cell body and at least one of the source and detector.

4. The sensor of claim wherein the window has a surface energy which matches the surface tension of the reagent solution to prevent bubble formation.

5. The sensor of claim 1 wherein the light source and detector are aligned along a cell axis.

6. The sensor of claim 1 wherein the detector is aligned in a direction substantially at a right angle to the light source.

7. The sensor of claim 1 further comprising a color filter between the cell body and at least one of the source and detector.

8. The sensor of claim 1 further comprising a focusing or collimating lens between the cell body and at least one of the source and detector.

9. The sensor of claim 1 wherein the species communication means comprises an open port.

10. The sensor of claim 1 further comprising a pair of space parallel membranes across the cell body and enclosing the sensing reagent.

11. The sensor of claim 1 wherein the sensing reagent is immobilized in the cell body.

12. The sensor of claim 1 wherein the modular cell body has a volume of about 10 to about 200 microliters.

13. The sensor of claim 1 wherein the light source is selected form a diode, laser and lamp.

14. The sensor of claim 1 wherein the light source is a light emitting diode.

15. The sensor of claim 14 wherein the detector is a photodiode.

16. The sensor of claim 1 wherein the light source is a lamp surrounded by a fiber optic bundle.

17. The sensor of claim 1 wherein the sensing reagent is selected from the group consisting of:
(a) phenol red, cresol red, methyl violet, congo red, phenolphthalein and bromcresol purple; pH sensitive absorption dyes and pH sensitive fluorescent dyes;
(b) the reagents of (a) in combination with eosin;
(c) fluorescein, acridine, umbelliferone and beta-naphthol;
(d) thorium-morin chelate, a luminol-$(NH_4)_2MoO_4$-$NH_4NO_3$ mixture, an ammonium molybdate/stannous chloride mixture and an N-ethyl-8-hydroxtetrahydroquinoline/ferric chloride mixture;
(e) a solvent for benzene with a lower refractive index than benzene;
(f) p-benzoquinone;
(g) cupric neocuprine;
(h) 2,2'-dipyridylketone hyrazone solution and lumpocupferron solution;
(i) a solvent for TCE with a lower refractive index than TCE;
(j) 2,2'-dipyridylketone hydrazone solution and indole-3-propionic acid;
(k) ferrozine;
(l) bis(2,4,6 trichlorophenyl) oxalate-$H_2O_2$-per-5ylene, acidified diphenylcarbazide, and a lphine/-KOH/$H_2O_2$ mixture;
(m) 2,3-diaminmonaphthalene, 3,3'-diaminobenzidine, and dithizone;
(n) 2,3 napthotriazole and a 1,10 phenanthroline/eosin mixture;
(o) butylrhodamine B/chloride mixture and 5-hydroxy-2-hydroxymethyl-1,4-pyrone;
(p) N-(4-methylumbelliferone-8-methyl)-1,10-diazo-18-crown-6;
q) p-nitrophenyl hydrazine;
(r) benzidine and tetramethyldiaminotriphenylmethane;
(s) acidified vanillin and an alcohol dehydrogenase/-zinc hydroxide mixture;
(t) dihydroacridane and indigo blue;
(u) Malachite green;
(v) red thorin-barium complex;
(w) a mixture of MM and BB monoclonal antibodies and MB polyclonal antibody tagged with a fluorescent compound;
(x) antibodies specific to cocaine, caffeine, chlordane, methadone, morphine, hepatitis and influenza;
(y) an enzyme selected form $3\alpha$-hydroxysteroid dehydrogenase, pyruvate dehydrogenase, aldehyde dehydrogenase and cholesterol dehydrogenase.

18. A reservoir chemical sensor comprising:
a modular reservoir cell body;
a sensing reagent in the cell body;
species communication means formed in the cell body for passing a species of interest into the cell body to interact with the sensing reagent;
a light source positioned at one end of the cell body to illuminate the interior of the cell body;
a detector positioned at an opposed end of the cell body and aligned with the light source along a cell axis top detect effects produced by the interaction of the species of interest with the sensing reagent;
at least one additional detector mounted to the cell body and aligned in a direction substantially at a right angle to the cell axis;
an adapter means for mounting and aligning each light source and detector to the cell body.

19. A reservoir chemical sensor comprising:
a modular reservoir cell body;
a sensing reagent in the cell body;
species communication means formed in the cell body for passing a species of interest into the cell body to interact with the sensing reagent wherein the species communication means comprises a flow-through port on a lateral surface of the cell body and a species-permeable, sensing-reagent-impermeable membrane across the flow-through port and a membrane retaining means for holding the membrane in place across the flow-through port and maintaining a liquid tight seal;
a light source positioned at one end of the cell body to illuminate the interior of the cell body;
a detector positioned at an opposed end of the cell body to detect effects produced by the interaction of the species of interest with the sensing reagent;
an adapter means at each end of the cell for mounting and aligning the light source and detector to the cell body;
wherein the membrane and sensing reagent are selected from the group consisting of the following combinations:
(a) the membrane is a hydrogen ion/hydronium ion permeable membrane and the sensing reagent is a pH sensitive absorption dye in combination with eosin;
(b) the membrane is an arsenic ion permeable membrane and the sensing reagent is selected from thorium-morin chelate, a luminol-$(NH_4)_2MoO_4$-$NH_4NO_3$ mixture, an ammonium molybdate/stannous chloride mixture and an N-ethyl-8-hydroxtetrahydroquinoline/ferric chloride mixture;
(c) the membrane is selected form high density polyethylene, high density polypropylene and fluorinated forms thereof, and the sensing reagent is a solvent for benzene with refractive index lower than benzene;
(d) the membrane is a cyanide permeabel membrane and the sensing reagent is p-benzene;

(e) the membrane is a hydrazine permeable membrane and the sensing reagent is cupric neocuprine solution;

(f) the membrane is a cupric ion permeable membrane and the sensing reagent is selected form 2,2'-dipyridylketone hydrazone solution and lumpocupferron solution;

(g) the membrane is a trichloroethylene permeable silicone polymer and the sensing reagent is a solvent for trichloroethylene with refractive index lower than trichloroethylene;

(h) the membrane is a mercuric ion permeable membrane and the sensing reagent is selected form 2,2'-dipyridylketone hydrazone solution and indole-3-propionic acid;

(i) the membrane is an iron(2+) permeable membrane and the sensing reagent is ferozine solution;

(j) the membrane is a chromium permeate membrane and the sensing reagent is selected from bis)2,4,6 trichlorophenyl) oxalate-$H_2O_2$-per-5ylene, acidified diphenycarbazide, and a lophine/KOH/$H_2O_2$ mixture;

(k) the membrane is a selenium permeable membrane and the sensing reagent is selected form 2,3 napthothriazole and a 1,10 phenanthroline/eosin mixture;

(m) the membrane is a gold permeable membrane and the sensing reagent is selected form butylrodamein B/chloride mixture and 5-hydrosy-2-hydroxmethyl-1,4-pyrone;

(n) the membrane is a calcium permeable membrane and the sensing reagent is N-(4methylumbelliferone-8-methyl)-1,10-diazo-18-crown-6;

20. The sensor of claim 19 further comprising a sample preparation chamber adjacent to the modular cell body and having the semi-permeable membrane as an interface between the sample preparation chamber and the cell body.

21. The senor of claim 20 wherein the sample preparation chamber has an inlet port and an outlet port for passing sample through the chamber and an irradiation port for irradiating the sample in the chamber.

22. The senor of claim 20 further comprising a chemical bed in the chamber for producing chemical reactions of the sample in the chamber.

23. The sensor of claim 19 further comprising a lateral sensing reagent inlet port and a lateral sensing reagent outlet port formed on a lateral surface in the cell body.

24. The sensor of claim 19 for arsenic wherein the membrane is an arsenic ion permeable membrane and the sensing solution is selected from thorium-morin chelate, a luminol-$(NH_4)_2MoO_4$-$NH_4NO_3$ mixture, an ammonium molybdate/stannous chloride mixture and an N-ethyl-8hydroxtetrahydroquinoline/ferric chloride mixture.

25. The sensor of claim 19 for benzene wherein the membrane is selected form high density polyethylene, high density polyproplene and fluoridated forms thereof, and the sensing reagent is a solvent for benzene with refractive index lower than benzene.

26. The sensor of claim 19 for cyanide wherein the membrane is a cyanide permeate membrane and the sensing reagent is p-benzoquinone.

27. The sensor of claim 19 for hydrazine wherein the membrane is a hydrazine permeable membrane and the sensing reagent is cupric neocuprine solution.

28. The sensor of claim 19 for cupric ion wherein the membrane is a cupric ion permeable membrane and the sensing reagent is selected for 2,2'- dipyridylketone hydrazone solution and lumpocupferron solution.

29. The sensor of claim 19 for trichloroethylene wherein the membrane is a trichloroethlene permeable silicone polymer and the sensing reagent is a solvent for trichloroethylene with refractive index lower than trichloroethylene.

30. The sensor of claim 29 wherein the solvent is ethanol or acetone.

31. The sensor of claim 19 for mercuric ion wherein the membrane is a mercuric ion permeate membrane and the sensing solution is selected form 2,2'-dipyridylketone hydrazone solution and indole-3-proionic acid.

32. The sensor of claim 19 for iron (2+) wherein the membrane is an iron (2+) permeable membrane and the sensing reagent is ferrozine solution.

33. The sensor of claim 19 for chromium wherein the membrane is a chromium permeable membrane and the sensing reagent is selected form bis(2,4,6 trichlorophenyl)oxalate-$H_2O_2$-per-5ylene, acidified diphenycarbazide, and a lophine/KOH/$H_2O_2$ mixture.

34. The sensor of claim 19 for selenium wherein the membrane is a selenium permeate membrane and the sensing reagent is selected from 2,3-diaminonaphthalene, 3,3'-diaminobezidine, and dithizone.

35. The sensor of claim 19 for silver wherein the membrane is a silver permeable membrane and the sensing reagent is selected from 2,3 napthotriazole and a 1,10 phenanthroline/eosin mixture.

36. The sensor of claim 19 for gold wherein the membrane is a gold permeable membrane and the sensing reagent is selected from butylrhodamine B/chloride and 5-hydroxy-2-hydroxmehtyl-1,4-pyrone.

37. The sensor of claim 19 for calcium wherein the membrane is a calcium permeable membrane and the sensing reagent is N-(4-methylumbelliferone-8-methyl) 1,10-diazo-18-crown-6.

38. The sensor of claim 19 for aldehydes wherein the membrane is an aldehyde permeable membrane and the sensing reagent is p-nitrophenyl hydrazine.

39. The sensor of claim 19 for blood wherein the membrane is a blood permeable membrane and the sensing reagent is selected from benzidine and tetramethyldiaminotriphenylmethane.

40. The sensor of claim 19 for alcohol wherein the membrane is an alcohol permeable membrane and the sensing reagent is selected from acidified vanillin and an alcohol dehydrogenase/zinc hydroxide mixture.

41. The sensor of claim 19 for ozone wherein the membrane is an ozone permeable membrane and the sensing reagent is selected from dihydroacridane and indigo blue.

42. The sensor of claim 19 for sulfite wherein the membrane is a sulfit porous membrane and the sensing reagent is malachite green.

43. The sensor of claim 19 for sulfate wherein the membrane is a sulfate porous membrane and the sensing reagent is ed thorin-barium complex.

44. The sensor of claim 19 for creatine phosphokinase wherein the membrane is a creatine phosphokinase permeable membrane and the sensing reagent is a mixture of MM, BB monclonal antibodies and MB polyclonal antibody.

45. A reservoir chemical sensor comprising:
a modular reservoir cell body;
a sensing reagent in the cell body;

species communication means formed in the cell body for passing a species of interest into the cell body to interact with the sensing reagent and comprising a lateral sample inlet port and an opposed lateral outlet port on opposed lateral surfaces of the cell body for passing sample through the cell body;

a lateral sensing reagent inlet port on a lateral surface of the cell body for replenishing reagent in the cell body;

valves placed in the inlet and outlet ports to regulate or control flow;

a light source positioned at one end of the cell body to illuminate the interior of the cell body;

a detector positioned at an opposed end of the cell body to detect effects produced by the interaction of the species of interest with the sensing reagent;

an adapter means at each end of the cell for mounting and aligning the light source and detector to the cell body.

46. A reservoir chemical sensor comprising:

a modular reservoir cell body comprising adjacent cell body sections and a semi-permeable membrane mounted between adjacent cell body sections to form adjacent cell body chambers;

a sensing reagent in the cell body;

species communication means formed in the cell body for passing a species of interest into the cell body to interact with the sensing reagent;

a light source positioned at one end of the cell body to illuminate the interior of the cell body;

a detector positioned at an opposed end of the cell body to detect effects produced by the interaction of the species of interest with the sensing reagent;

an adapter means at each end of the cell for mounting and aligning the light source and detector to the cell body;

wherein the sensing reagent further comprises a first reagent in one cell body chamber and a second reagent in a second cell body chamber, wherein the first reagent is reactive with the species of interest to form a reaction product, and the second reagent is reactive to the reaction product, and the membrane is permeable to the reaction product and impermeable to the first and second reagents.

47. The sensor of claim 46 wherein the light source and detector are positioned in the second chamber.

48. The sensor of claim 46 wherein the species communication means are formed in the first chamber.

49. The sensor of claim 46 for arsenic wherein the first reagent is ammonium molybdate and the second reagent is stannous chloride.

50. The sensor of claim 46 for arsenic wherein the first reagent is N-ethyl-8-hydroxtetrahydroquinoline and the second reagent is ferric chloride.

* * * * *